US011709747B2

(12) United States Patent
Hresko et al.

(10) Patent No.: US 11,709,747 B2
(45) Date of Patent: Jul. 25, 2023

(54) PATIENT ASSURANCE SYSTEM AND METHOD

(71) Applicant: ZOLL Medical Corporation, Chelmsford, MA (US)

(72) Inventors: Patrick Hresko, Mount Pleasant, PA (US); Thomas E. Kaib, Irwin, PA (US); Trisha A. Pavel, Pittsburgh, PA (US); Grace Owens, Pittsburgh, PA (US); John Clark, Pittsburgh, PA (US); Rachel Carlson, Falls Creek, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 385 days.

(21) Appl. No.: 15/397,102

(22) Filed: Jan. 3, 2017

(65) Prior Publication Data

US 2017/0199797 A1 Jul. 13, 2017

Related U.S. Application Data

(60) Provisional application No. 62/276,612, filed on Jan. 8, 2016.

(51) Int. Cl.
*G06F 11/30* (2006.01)
*A61B 5/00* (2006.01)
(Continued)

(52) U.S. Cl.
CPC ........ *G06F 11/3013* (2013.01); *A61B 5/0002* (2013.01); *A61B 5/0022* (2013.01);
(Continued)

(58) Field of Classification Search
CPC ........... G06Q 50/22–24; G06F 11/3013; G06F 11/3055; A61B 5/318; A61B 5/0002; A61B 5/0022; A61B 5/6804; A61B 5/7425
See application file for complete search history.

(56) References Cited

U.S. PATENT DOCUMENTS 199,797 A * 1/1878 Hresko et al. .......... B24B 31/02
451/328
3,922,665 A 11/1975 Curry et al.
(Continued)

FOREIGN PATENT DOCUMENTS

EP 707825 A2 4/1996
EP 761255 A1 3/1997
(Continued)

OTHER PUBLICATIONS

Fuertes B, Toquero J, Arroyo-Espliguero R, Lozano IF. Pacemaker lead displacement: mechanisms and management. Indian Pacing Electrophysiol J. Oct. 1, 2003;3(4):231-8. PMID: 16943923; PMCID: PMC1513524. (Year: 2003).*

(Continued)

*Primary Examiner* — Joshua B Blanchette

(74) *Attorney, Agent, or Firm* — Finch & Maloney PLLC

(57) ABSTRACT

In one example, an ambulatory medical device is provided. The ambulatory medical device includes a plurality of subsystems, at least one sensor configured to acquire data descriptive of a patient, a user interface and at least one processor coupled to the at least one sensor and the user interface. The at least one processor is configured to identify subsystem status information descriptive of an operational status of each subsystem of the plurality of subsystems and to provide a device health report for the ambulatory medical device via the user interface, the device health report being based on the operational status of each subsystem.

26 Claims, 20 Drawing Sheets

(51) Int. Cl.
*G16H 40/40* (2018.01)
*G16H 10/60* (2018.01)
*G16H 40/67* (2018.01)
*A61B 5/318* (2021.01)
*A61N 1/04* (2006.01)
*A61B 5/276* (2021.01)
*G16H 20/30* (2018.01)
*A61N 1/39* (2006.01)

(52) U.S. Cl.
CPC ............ *A61B 5/318* (2021.01); *A61B 5/6804* (2013.01); *A61B 5/6831* (2013.01); *A61B 5/7425* (2013.01); *G06F 11/3055* (2013.01); *G16H 10/60* (2018.01); *G16H 20/30* (2018.01); *G16H 40/40* (2018.01); *G16H 40/67* (2018.01); *A61B 5/276* (2021.01); *A61N 1/046* (2013.01); *A61N 1/0484* (2013.01); *A61N 1/3904* (2017.08); *A61N 1/3993* (2013.01)

(56) References Cited

U.S. PATENT DOCUMENTS

| | | |
|---|---|---|
| 4,576,170 A | 3/1986 | Bradley et al. |
| 4,580,572 A | 4/1986 | Granek et al. |
| 4,583,547 A | 4/1986 | Granek et al. |
| 4,729,377 A | 3/1988 | Granek et al. |
| 4,928,690 A | 5/1990 | Heilman et al. |
| 4,991,217 A | 2/1991 | Garrett et al. |
| 5,078,134 A | 1/1992 | Heilman et al. |
| 5,348,008 A | 9/1994 | Bomn et al. |
| 5,371,692 A | 12/1994 | Draeger et al. |
| 5,381,798 A | 1/1995 | Burrows |
| 5,645,571 A | 7/1997 | Olson et al. |
| 5,741,306 A | 4/1998 | Glegyak et al. |
| 5,749,913 A | 5/1998 | Cole |
| 5,879,374 A | 3/1999 | Powers et al. |
| 5,899,925 A | 5/1999 | Ochs et al. |
| 5,929,601 A | 7/1999 | Kaib et al. |
| 5,919,212 A | 8/1999 | Olson et al. |
| 5,944,669 A | 8/1999 | Kaib |
| 6,065,154 A | 5/2000 | Hulings et al. |
| 6,097,982 A | 8/2000 | Glegyak et al. |
| 6,253,099 B1 | 6/2001 | Oskin et al. |
| 6,280,461 B1 | 8/2001 | Glegyak et al. |
| 6,304,780 B1 | 10/2001 | Owen et al. |
| 6,336,900 B1 | 1/2002 | Alleckson et al. |
| 6,374,138 B1 | 4/2002 | Owen et al. |
| 6,390,996 B1 | 5/2002 | Halperin et al. |
| 6,406,426 B1 | 6/2002 | Reuss et al. |
| 6,418,346 B1 | 7/2002 | Nelson et al. |
| 6,442,433 B1 | 8/2002 | Linberg |
| 6,546,285 B1 | 4/2003 | Owen et al. |
| 6,602,191 B2 | 8/2003 | Quy |
| 6,668,192 B1* | 12/2003 | Parker ............... A61N 1/39 600/522 |
| 6,681,003 B2 | 1/2004 | Linder et al. |
| 6,694,191 B2 | 2/2004 | Startweather et al. |
| 6,804,554 B2 | 10/2004 | Ujhelyi et al. |
| 6,865,413 B2 | 3/2005 | Halperin et al. |
| 6,889,078 B2 | 5/2005 | Struble et al. |
| 6,889,079 B2 | 5/2005 | Bocek et al. |
| 6,908,437 B2 | 6/2005 | Bardy |
| 7,088,233 B2 | 8/2006 | Menard |
| 7,108,665 B2 | 9/2006 | Halperin et al. |
| 7,149,579 B1 | 12/2006 | Koh et al. |
| 7,220,235 B2 | 5/2007 | Geheb et al. |
| 7,295,871 B2 | 11/2007 | Halperin et al. |
| 7,340,296 B2 | 3/2008 | Stahmann et al. |
| 7,353,063 B2* | 4/2008 | Simms, Jr. ......... A61N 1/37282 607/30 |
| 7,439,705 B2 | 10/2008 | Koike |
| 7,453,354 B2 | 11/2008 | Reiter et al. |
| 7,476,206 B2 | 1/2009 | Palazzolo et al. |
| 7,488,293 B2 | 2/2009 | Marcovecchio et al. |
| 7,627,372 B2 | 12/2009 | Vaisnys et al. |
| 7,712,373 B2 | 5/2010 | Nagle et al. |
| 7,827,005 B2 | 11/2010 | Kimball |
| 7,831,303 B2 | 11/2010 | Rueter et al. |
| 7,913,015 B2* | 3/2011 | Kallmyer ............... G06F 13/14 710/110 |
| 7,953,478 B2 | 5/2011 | Vaisnys et al. |
| 7,974,689 B2 | 7/2011 | Volpe et al. |
| 7,991,460 B2 | 8/2011 | Fischell et al. |
| 8,005,552 B2 | 8/2011 | Covey et al. |
| 8,121,683 B2 | 2/2012 | Bucher et al. |
| 8,140,154 B2 | 3/2012 | Donnelly et al. |
| 8,224,441 B2 | 7/2012 | Vaisnys et al. |
| 8,234,128 B2* | 7/2012 | Martucci ............... A61B 5/0002 705/2 |
| 8,271,082 B2 | 9/2012 | Donnelly et al. |
| 8,319,632 B1 | 11/2012 | Vaisnys et al. |
| 8,334,768 B2* | 12/2012 | Eaton .................. H04W 4/029 340/539.13 |
| 8,369,944 B2 | 2/2013 | Macho et al. |
| 8,406,842 B2 | 3/2013 | Kaib et al. |
| 8,475,367 B1* | 7/2013 | Yuen .................. G06F 19/3418 600/300 |
| 8,494,628 B2 | 7/2013 | Vaisnys et al. |
| 8,644,925 B2 | 2/2014 | Volpe et al. |
| 8,649,861 B2 | 2/2014 | Donnelly et al. |
| 8,676,313 B2 | 3/2014 | Volpe et al. |
| 8,706,215 B2 | 4/2014 | Kaib et al. |
| 8,768,441 B2 | 7/2014 | DeZwart et al. |
| 8,774,917 B2 | 7/2014 | Macho et al. |
| 8,781,577 B2 | 7/2014 | Freeman et al. |
| 8,880,196 B2 | 11/2014 | Kaid |
| 8,897,860 B2 | 11/2014 | Volpe et al. |
| 8,904,214 B2 | 12/2014 | Volpe et al. |
| 9,283,399 B2 | 3/2016 | Donnelly et al. |
| 10,029,108 B2 | 7/2018 | Power et al. |
| 10,272,010 B2 | 4/2019 | Freeman et al. |
| 10,426,342 B2 | 10/2019 | Hresko et al. |
| 10,561,852 B2 | 2/2020 | Murphy et al. |
| 10,744,057 B2 | 8/2020 | Freeman et al. |
| 11,202,569 B2 | 12/2021 | Hresko et al. |
| 11,213,211 B2 | 1/2022 | Freeman et al. |
| 2001/0031991 A1 | 10/2001 | Russial |
| 2002/0052539 A1 | 5/2002 | Haller |
| 2002/0181680 A1 | 12/2002 | Linder et al. |
| 2003/0004547 A1 | 1/2003 | Owen et al. |
| 2003/0032988 A1 | 2/2003 | Fincke |
| 2003/0095648 A1 | 5/2003 | Kaib et al. |
| 2003/0212311 A1 | 11/2003 | Nova et al. |
| 2004/0049233 A1 | 3/2004 | Edwards |
| 2005/0131465 A1 | 6/2005 | Freeman et al. |
| 2005/0246199 A1 | 11/2005 | Futch |
| 2005/0283198 A1 | 12/2005 | Haubrich et al. |
| 2006/0015148 A1 | 1/2006 | McCabe et al. |
| 2006/0059976 A1 | 3/2006 | Simonenko et al. |
| 2006/0095091 A1 | 5/2006 | Drew |
| 2006/0136000 A1 | 6/2006 | Bowers |
| 2006/0211934 A1 | 9/2006 | Hassonjee et al. |
| 2006/0259080 A1 | 11/2006 | Vaisnys et al. |
| 2007/0129769 A1 | 6/2007 | Bourget et al. |
| 2007/0232946 A1 | 10/2007 | Field et al. |
| 2008/0033495 A1 | 2/2008 | Kumar |
| 2008/0058884 A1 | 3/2008 | Matos |
| 2008/0097791 A1 | 4/2008 | Alsafadi |
| 2008/0097793 A1 | 4/2008 | Dicks et al. |
| 2008/0103402 A1 | 5/2008 | Stickney et al. |
| 2008/0249591 A1 | 10/2008 | Gaw et al. |
| 2008/0287749 A1 | 11/2008 | Reuter |
| 2008/0306560 A1 | 12/2008 | Macho et al. |
| 2008/0306562 A1 | 12/2008 | Donnelly et al. |
| 2008/0312709 A1 | 12/2008 | Volpe et al. |
| 2009/0058635 A1 | 3/2009 | LaLonde et al. |
| 2009/0073991 A1 | 3/2009 | Landrum et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076346 A1 | 3/2009 | James et al. |

(56) References Cited

U.S. PATENT DOCUMENTS

| | | |
|---|---|---|
| 2009/0076349 A1 | 3/2009 | Libbus et al. |
| 2009/0076350 A1 | 3/2009 | Bly et al. |
| 2009/0076363 A1 | 3/2009 | Bly et al. |
| 2009/0076559 A1 | 3/2009 | Libbus et al. |
| 2009/0146822 A1 | 6/2009 | Soliman |
| 2009/0234410 A1 | 9/2009 | Libbus et al. |
| 2009/0264792 A1 | 10/2009 | Mazar |
| 2009/0292194 A1 | 11/2009 | Libbus et al. |
| 2009/0312650 A1 | 12/2009 | Maile et al. |
| 2010/0010559 A1 | 1/2010 | Zhang et al. |
| 2010/0052892 A1 | 3/2010 | Allen et al. |
| 2010/0069735 A1 | 3/2010 | Berkner |
| 2010/0076533 A1 | 3/2010 | Dar et al. |
| 2010/0295674 A1 | 11/2010 | Hsieh et al. |
| 2010/0298899 A1 | 11/2010 | Donnelly et al. |
| 2010/0312297 A1 | 12/2010 | Volpe et al. |
| 2011/0022105 A9 | 1/2011 | Owen et al. |
| 2011/0093840 A1 | 4/2011 | Pynenburg et al. |
| 2011/0096384 A1 | 4/2011 | Pynenburg et al. |
| 2011/0098765 A1 | 4/2011 | Patel |
| 2011/0170692 A1 | 7/2011 | Konrad et al. |
| 2011/0172550 A1 | 7/2011 | Konrad et al. |
| 2011/0288604 A1 | 11/2011 | Kaib et al. |
| 2011/0288605 A1 | 11/2011 | Kaib et al. |
| 2012/0011382 A1 | 1/2012 | Volpe et al. |
| 2012/0112903 A1 | 5/2012 | Kaib et al. |
| 2012/0146797 A1 | 6/2012 | Oskin et al. |
| 2012/0150008 A1 | 6/2012 | Kaib et al. |
| 2012/0158075 A1 | 6/2012 | Kaib et al. |
| 2012/0191476 A1 | 7/2012 | Reid et al. |
| 2012/0277642 A1 | 11/2012 | Smith et al. |
| 2012/0277645 A1 | 11/2012 | Kikuta et al. |
| 2012/0283794 A1 | 11/2012 | Kaib et al. |
| 2012/0289809 A1 | 11/2012 | Kaib et al. |
| 2012/0293323 A1 | 11/2012 | Kaib et al. |
| 2012/0302860 A1 | 11/2012 | Volpe et al. |
| 2013/0013014 A1 | 1/2013 | Donnelly et al. |
| 2013/0060149 A1 | 3/2013 | Song et al. |
| 2013/0066653 A1* | 3/2013 | Joao ............... A61N 1/37211 705/3 |
| 2013/0085538 A1 | 4/2013 | Volpe et al. |
| 2013/0113496 A1 | 5/2013 | Craig, III et al. |
| 2013/0144355 A1 | 6/2013 | Macho et al. |
| 2013/0218252 A1 | 8/2013 | Kaib et al. |
| 2013/0231711 A1 | 9/2013 | Kaib |
| 2013/0324868 A1 | 12/2013 | Kaib et al. |
| 2013/0325078 A1 | 12/2013 | Whiting et al. |
| 2013/0325096 A1 | 12/2013 | Dupelle et al. |
| 2014/0004814 A1 | 1/2014 | Elghazzawi |
| 2014/0031884 A1 | 1/2014 | Elghazzawi |
| 2014/0031885 A1 | 1/2014 | Elghazzawi |
| 2014/0046391 A1* | 2/2014 | Cowan ............... G16H 40/63 607/5 |
| 2014/0163334 A1 | 6/2014 | Volpe et al. |
| 2014/0206974 A1 | 7/2014 | Volpe et al. |
| 2014/0249613 A1 | 9/2014 | Kaib et al. |
| 2014/0266718 A1 | 9/2014 | Bongberg |
| 2014/0277243 A1 | 9/2014 | Maskara et al. |
| 2014/0288609 A1 | 9/2014 | Freeman et al. |
| 2014/0288610 A1 | 9/2014 | Freeman et al. |
| 2014/0303680 A1 | 10/2014 | Donnelly et al. |
| 2014/0324112 A1 | 10/2014 | Macho et al. |
| 2014/0336514 A1 | 11/2014 | Peyman |
| 2014/0379255 A1 | 12/2014 | Johnson |
| 2015/0005588 A1 | 1/2015 | Herken |
| 2015/0035654 A1 | 2/2015 | Kaib et al. |
| 2015/0037636 A1 | 2/2015 | Amsler et al. |
| 2015/0039039 A1 | 2/2015 | Macho et al. |
| 2015/0039042 A1 | 2/2015 | Amsler et al. |
| 2015/0039053 A1 | 2/2015 | Kaib et al. |
| 2015/0080699 A1 | 3/2015 | Kaib et al. |
| 2015/0224330 A1 | 8/2015 | Kaib et al. |
| 2015/0321022 A1* | 11/2015 | Sullivan ............... A61N 1/0484 607/5 |
| 2016/0015986 A1* | 1/2016 | Seeberger ............ A61N 1/3718 607/28 |
| 2016/0274162 A1 | 9/2016 | Freeman et al. |
| 2017/0065823 A1 | 3/2017 | Kaib et al. |
| 2017/0199797 A1 | 7/2017 | Hresko et al. |

FOREIGN PATENT DOCUMENTS

| | | |
|---|---|---|
| JP | 11149379 | 6/1999 |
| JP | 2002509472 A | 3/2002 |
| JP | 2002-514107 A | 5/2002 |
| JP | 2004318839 | 11/2004 |
| JP | 2006091013 A | 4/2006 |
| JP | 2008302225 A | 12/2008 |
| JP | 2008302228 A | 12/2008 |
| JP | 2009510631 A | 3/2009 |
| JP | 2009521865 A | 6/2009 |
| JP | 2009528909 | 8/2009 |
| JP | 2012003311 A | 1/2012 |
| WO | 83/04171 A1 | 12/1983 |
| WO | 1997022297 A1 | 6/1997 |
| WO | 1998039061 A2 | 9/1998 |
| WO | 2000030529 A1 | 6/2000 |
| WO | 2004078259 A1 | 9/2004 |
| WO | 2007019325 A2 | 2/2007 |
| WO | 2009034506 A1 | 3/2009 |
| WO | 2009122277 A2 | 10/2009 |
| WO | 2011027459 A1 | 3/2011 |
| WO | 2012006524 A1 | 1/2012 |
| WO | 2012100219 A1 | 7/2012 |
| WO | 2012149482 A2 | 11/2012 |
| WO | 2013040214 A1 | 3/2013 |
| WO | 2013130957 A2 | 9/2013 |
| WO | 2014018057 A1 | 1/2014 |
| WO | 2014018160 A1 | 1/2014 |
| WO | 2014097035 A1 | 6/2014 |
| WO | 2014099986 A1 | 6/2014 |

OTHER PUBLICATIONS

American Journal of Respiratory and Critical Care Medicine, vol. 166, pp. 111-117 (2002), American Thoracic Society, ATS Statement: Guidelines for the Six-Minute Walk Test, available at http://ajrccm.atsjournals.org/cgi/content/ull/166/1/111.

http://web.archive.org/web/20030427001846/http:/www.lifecor.comiimagelib/imageproduct.asp. Published by LifeCor, Inc., 2002, on a webpage owned by LifeCor, Inc.

Association for the Advancement of Medical Instrumentation, ANSI/AAMI DF80:2003, Medical Electrical Equipment—Part 2-4: Particular Requirements for the Safety of Cardiac Defibrillators (including Automated External Defibrillators) 2004, ISBN 1-57020-210-9; abstract; p. vi; p. 50, section 107.1.2.

ZOLL Medical Corporation, LifeVest Model WCD 3000 Operator's Manual, Pittsburgh, PA.

International Search Report and Written Opinion from PCT/US2013/028598 dated May 9, 2013.

PCT Search Report and Written Opinion for PCT Application No. PCT/US2016/023057 dated Sep. 6, 2016, 14 pages.

* cited by examiner

| Non-Exhaustive List of Example Triggering Events for Self-Tests |
|---|
| 1. Initialization and Baselining; |
| 2. Download of Patient Profile; |
| 3. Button(s) Actuation Detection; |
| 4. Mechanical Impact Detection; |
| 5. Remotely Initiated Self-Test(s); |
| 6. Execution-Time Download Self-Test(s); |
| 7. Assembly/Disassembly Sensing; |
| 8. Round Robin Testing; |
| 9. Serialized Mismatch Detection; |
| 10. Current Sensing; |
| 11. Temperature Sensing; |
| 12. Moisture Sensing; |
| 13. Gas Gauge Level Sensing; |
| 14. Battery Voltage Level Detection; |
| 15. Critical Error Handling; |
| 16. Battery Replacement; |
| 17. Electrode / Therapy Pad Placement Sensing; |
| 18. Countdown Timer; |
| 19. Multi-tasking; |
| 20. User Activity; |
| 21. Post Shock Delivery; |
| 22. Upload or Download of Data; |
| 23. Pressure Sensing; |
| 24. Ambient Pressure; |
| 25. Excess Strain Detection; |
| 26. Tampering; |
| 27. any combination of the above. |

FIG. 9

| Non-Exhaustive List of Example Self-Tests; |
|---|
| 1. Battery Capacity; |
| 2. Remaining Battery Run Time; |
| 3. Battery Status; |
| 4. Status of User Response Buttons; |
| 5. Determine if ECG Monitoring Signal Quality Is Compromised by Noise or Electrode Fall-off; |
| 6. ECG Signal Intensity; |
| 7. Confirm Detection Algorithm Parameters, Therapy Electrode Placement and Impedance Levels; |
| 8. Operation of Various Electrical Components, Subsystems, or Systems, for example, a DC-DC Converter; |
| 9. Background Checks of inputs and Outputs (I'0); |
| 10. Tests of Battery Voltage, Capacitor Voltage, and or DC-DC Converter; |
| 11. System-wide Tests, such as Testing Battery Power Consumption, Battery Voltage Changing Faster/Slower than it shows, One or More Individual Component Checks, like Internal Resistance of the Battery, and the like; |
| 12. Looking at Values of Individual Parts; |
| 13. Microprocessor Self-Test; |
| 14. Gate Array Test; |
| 15. System Monitor Test; |
| 16. CRC Test; |
| 17. RAM/ROM Test; |
| 18. Watchdog Timer Test; |
| 19. Removable Memory Card Test; |
| 20. Electrode Test; |
| 21. Battery Test; |
| 22. Battery Charging Test; |
| 23. Power Converter Test; |
| 24. Capacitor Charge Retention Test; |
| 25. Capacitor Charge/Discharge Test; |
| 26. Patient Discharge Resistor Test; |
| 27. Shock Discharge Test; |
| 28. Therapy Electrode Pad Cell ' Bladder Integrity Test; |
| 29. Electrode 1 Therapy Pad Placement Test; |
| 30. User Interface Test; |
| 31. Round Robin Testing; |
| 32. any combination of the above. |

FIG. 10

| Subsystem | Test |
|---|---|
| battery subsystem | Battery Capacity |
| battery subsystem | Remaining Battery Run Time |
| battery subsystem | Battery Status |
| battery subsystem | System-wide Tests, such as Testing Battery Power Consumption, Battery Voltage Changing Faster Slower than it shows. One or More Individual Component Checks, like Internal Resistance of the Battery, and the like; |
| battery subsystem | Battery Test |
| battery subsystem monitor subsystem | Round Robin Testing |
| battery subsystem monitor subsystem | Tests of Battery Voltage, Capacitor Voltage, and/or DC-DC Converter |
| battery subsystem monitor subsystem | Capacitor Charge/Discharge Test |
| monitor subsystem | Status of User Response Buttons |
| monitor subsystem | Operation of Various Electrical Components, Subsystems, or Systems, for example, a DC-DC Converter |
| monitor subsystem | Confirm Detection Algorithm Parameters. Therapy Electrode Placement and Impedance Levels |
| monitor subsystem | Background Checks of Inputs and Outputs (I/O) |
| monitor subsystem | Microprocessor Self-Test |
| monitor subsystem | Gate Array Test |
| monitor subsystem | System Monitor Test |
| monitor subsystem | CRC Test |
| monitor subsystem | RAM/ROM Test |
| monitor subsystem | Watchdog Timer Test |
| monitor subsystem | Removable Memory Card Test |
| monitor subsystem | Power Converter Test |
| monitor subsystem | Capacitor Charge Retention Test |
| monitor subsystem | Shock Discharge Test |
| monitor subsystem | User Interface Test |
| electrode subsystem | Determine if ECG Monitoring Signal Quality Is Compromised by Noise or Electrode Fall-off |
| electrode subsystem | ECG Signal Intensity |
| electrode subsystem | Patient Discharge Resistor Test |
| electrode subsystem | Electrode Test |
| electrode subsystem | Therapy Electrode Pad Cell - Bladder Ingetrity Test |
| electrode subsystem | Electrode 1 Therapy Pad Placement Test |
| base station subsystem | Battery Charging Test |
| communications subsystem | Network Connectivity Test |
| any subsystem | Looking at Values of Individual Parts |

FIG. 11

PATIENT ASSURANCE SYSTEM AND METHOD

CROSS-REFERENCE TO RELATED APPLICATIONS

This application claims priority under 35 U.S.C. § 119(e) to U.S. Provisional Application Ser. No. 62/276,612, titled "PATIENT ASSURANCE SYSTEM AND METHOD," filed on Jan. 8, 2016, which is herein incorporated by reference in its entirety.

NOTICE OF MATERIAL SUBJECT TO COPYRIGHT PROTECTION

Portions of the material in this patent document are subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

This disclosure relates generally to external medical devices, and more specifically, to apparatus and processes that communicate information regarding the operational status of a medical device.

There are a wide variety of electronic and mechanical medical devices for monitoring and treating patients' medical conditions. The one or more particular medical devices used to monitor and/or treat a patient depend on the underlying medical condition with which the patient is afflicted. For example, where a patient has a medical condition that affects the patient's cardiac function (e.g., a cardiac arrhythmia), medical devices such as cardiac pacemakers or defibrillators may be used to treat the patient. In some cases, these medical devices may be surgically implanted or externally connected to the patient. Such medical devices may be used alone, or in combination with drug therapies, to treat medical conditions such as cardiac arrhythmias.

One of the most deadly cardiac arrhythmias is ventricular fibrillation, which occurs when normal, regular electrical impulses are replaced by irregular and rapid impulses, causing the heart muscle to stop normal contractions and to begin to quiver. Normal blood flow ceases, and organ damage or death can result in minutes if normal heart contractions are not restored. Because the victim has no perceptible warning of the impending fibrillation, death often occurs before the necessary medical assistance can be administered. Other cardiac arrhythmias include excessively slow heart rates known as bradycardia.

Implantable or external pacemakers and defibrillators (such as automated external defibrillators or AEDs) have significantly improved the ability to treat these otherwise life-threatening conditions. Such devices operate by applying corrective electrical pulses directly to the patient's heart. For example, bradycardia can be corrected through the use of an implanted or external pacemaker device. Ventricular fibrillation can be treated by an implanted or external defibrillator.

Some medical devices operate by continuously or substantially continuously monitoring the patient's heart for treatable arrhythmias via one or more sensing electrodes and, when such is detected, applying corrective electrical pulses directly to the heart through one or more therapy electrodes.

SUMMARY

Medical devices play an important role in many treatment regimens prescribed to patients. Often these medical devices are complex instruments, having sundry subsystems, components, and configuration options. The importance and complexity of medical devices can lead to anxiety in patients, who have little knowledge regarding how the medical devices operate and, therefore, little ability to verify that the medical devices are operating properly. This anxiety and lack of understanding can contribute to undesirable behavior in patients. For instance, a patient may call support frequently, attempting to gain reassurance that a medical device is operating properly. In other instances, a patient may be intimidated by the device, and avoid calling support, even where the medical device is in need of maintenance, repair, or replacement.

Aspects and examples disclosed herein manifest an appreciation for these and other problems facing patients and medical device providers. For instance, some aspects and examples are directed to apparatus and processes that generate and provide information regarding the readiness of a medical device to perform one or more operations. According to these aspects and examples, a medical device includes hardware and/or software components that assess the operability of the medical device and one or more subsystems of the medical device. After executing this assessment, the components generate, store, and provide one or more reports describing the operability of the medical device and its one or more subsystems. These reports may be rendered in a variety of formats, including textual, graphical, and auditory. To enable patients and other users to obtain these reports as desired, the hardware and/or software components may be executed on-demand and the resulting reports accessed via a variety of communications channels.

In one example, an ambulatory medical device is provided. The ambulatory medical device includes a plurality of subsystems, at least one sensor configured to acquire data descriptive of a patient, a user interface and at least one processor coupled to the at least one sensor and the user interface. The at least one processor is configured to identify subsystem status information descriptive of an operational status of each subsystem of the plurality of subsystems and to provide a device health report for the ambulatory medical device via the user interface, the device health report being based on the operational status of each subsystem.

In the ambulatory medical device, the plurality of subsystems may include at least one of a monitor subsystem, an electrode subsystem, a battery subsystem, a base station subsystem, a garment subsystem, and a communications subsystem. The base station subsystem may include a battery charger subsystem and at least one of a base station user interface subsystem and the communications subsystem. The base station subsystem and/or the monitor subsystem may include the communication subsystem. The electrode subsystem and/or the garment subsystem may include a sensing electrode subsystem, a therapy electrode subsystem, and/or a gel deployment subsystem. The electrode subsystem may include the garment subsystem. The monitor subsystem may include at least one of a sensor interface, a therapy delivery interface, and/or a processing subsystem. The monitor subsystem, the electrode subsystem, the garment subsystem, and/or the battery subsystem may include an energy storage and delivery subsystem.

In the ambulatory medical device, the subsystem status information may include a plurality of indications, each indication of the plurality of indications being associated with a subsystem of the plurality of subsystems and indicating whether the subsystem associated with the indication is in an operational state or a nonoperational state. In the ambulatory medical device, the device health report may be configured to indicate to a user whether each subsystem of the plurality of subsystems is in an operational state or a nonoperational state based on an indication of the plurality of indications that is associated with the subsystem. The device health report may be configured to notify a user whether each subsystem of the plurality of subsystems is in an operational state or a nonoperational state based on an indication of the plurality of indications that is associated with the subsystem. The device health report may include one or more visual user interface elements that provide one or more visual indications of whether each subsystem of the plurality of subsystems is in an operational state or a nonoperational state based on an indication of the plurality of indications that is associated with the subsystem. The one or more visual user interface elements may include selectable visual user interface elements configured to receive input from a user. In the ambulatory medical device, the user interface may include an audio output component and the device health report may be configured to be rendered in audio format via the audio output component. The device health report may include at least one of icons, animation, video, and textual information relating to a corresponding one of the plurality of the subsystems. The user interface may be integral to a remote device distinct from the medical device. The user interface may include an email client.

In the ambulatory medical device, the user interface may include one or more user interface elements configured to activate under control of the at least one processor, and the at least one processor may be configured to provide the device health report at least in part by signaling the one or more user interface elements to activate. For example, the one or more user interface elements can include visual elements such as one or more light emitting diodes (LEDs), lights, display screens, or other visual indicators that can be caused to activate on receipt of an appropriate signal. For example, the visual elements may change from an unilluminated state to an illuminated state, change display color (e.g., from green to red), or change display pattern (e.g., steady light to flashing light at a predetermined rate) when activated. It is understood that various other modes of visually signaling the underlying device health state may be implemented. Additionally or alternatively, the user interface may include one or more audio elements configured to emit sound under control of the at least one processor and the at least one processor may be configured to provide the device health report at least in part by signaling the one or more audio elements to emit sound. For example, the emitted sound may be a tone or a series of tones. In some cases, a voice synthesizer may be provided to deliver the device health report verbally to the patient. For example, an audible message may include a warning to the patient, a caregiver, or other surrogate to "CHECK ELECTRODES" on determining that the one or that the electrodes subsystem needs attention due to an underlying problem.

In one example, a report distribution system is provided. The report distribution system includes a remote server and an ambulatory medical device. The ambulatory medical device includes a plurality of subsystems comprising at least one sensor configured to acquire data descriptive of a patient, a network interface configured to communicate with the remote server, and at least one processor coupled to the at least one sensor and the network interface. The at least one processor is configured to identify subsystem status information descriptive of an operational status of each subsystem of the plurality of subsystems and to provide a device health report for the ambulatory medical device to the remote server via the network interface, the device health report being based on the operational status of each subsystem.

In the report distribution system, the plurality of subsystems may include at least one of a monitor subsystem, an electrode subsystem, a battery subsystem, a base station subsystem, a garment subsystem, and a communications subsystem. The base station subsystem may include a battery charger subsystem and at least one of a base station user interface subsystem and the communication subsystem. The base station subsystem and/or the monitor subsystem may include the communication subsystem. The electrode subsystem and/or the garment subsystem may include a sensing electrode subsystem, a therapy electrode subsystem, and/or a gel deployment subsystem. The electrode subsystem may include the garment subsystem. The monitor subsystem may include at least one of a sensor interface, a therapy delivery interface, and/or a processing subsystem. The monitor subsystem, the electrode subsystem, the garment subsystem, and/or the battery subsystem may include an energy storage and delivery subsystem.

In the report distribution system, the subsystem status information may include a plurality of indications, each indication of the plurality of indications being associated with a subsystem of the plurality of subsystems and indicating whether the subsystem associated with the indication is in an operational state or a nonoperational state. In the report distribution system, the device health report may be configured to indicate to a user whether each subsystem of the plurality of subsystems is in an operational state or a nonoperational state based on an indication of the plurality of indications that is associated with the subsystem. The device health report may be configured to notify a user whether each subsystem of the plurality of subsystems is in an operational state or a nonoperational state based on an indication of the plurality of indications that is associated with the subsystem. The device health report may include one or more visual user interface elements that provide one or more visual indications of whether each subsystem of the plurality of subsystems is in an operational state or a nonoperational state based on an indication of the plurality of indications that is associated with the subsystem. The one or more visual user interface elements may include selectable visual user interface elements configured to receive input from a user.

In the report distribution system, the user interface may include an audio output component and the device health report is configured to be rendered in audio format via the audio output component. The device health report may include at least one of icons, animation, video, and textual information relating to a corresponding one of the plurality of the subsystems. The user interface is integral to a remote device distinct from the ambulatory medical device, the device being configured to communicate with at least one of the ambulatory medical device and the remote server. The user interface may include an email client. The remote device may include a base station subsystem comprising a base station user interface configured to provide the device health report.

In one example, an ambulatory medical device is provided. The ambulatory medical device includes at least one sensor configured to acquire data descriptive of a patient, a user interface, and at least one processor in communication with the at least one sensor and the user interface. The at least one processor is configured to provide, via the user interface, an element selectable by the patient; to receive, via the user interface, input selecting of the element; and to provide, in response to receiving the input, output indicating an ability of the ambulatory medical device to perform one or more operations.

In the ambulatory medical device, the one or more operations may include at least one of cardiac arrhythmia detection, gel deployment, treatment sequence execution, alarm issuance, baselining execution, patient information transfer, button actuation detection, mechanical impact detection, self-test initiation, temperature detection, and battery voltage level detection. In the ambulatory medical device, the element may include at least one of a virtual button, a physical button, a plurality of virtual buttons, a plurality of physical buttons, a microphone, and a switch. In the ambulatory medical device, the input may include a threshold number of actuations of the element within a predetermined time period.

In the ambulatory medical device, the at least one processor may be configured to provide the output at least in part by displaying the output via the user interface or transmitting the output to a remote device. The at least one processor may be configured to transmit the output to a remote device at least in part by being configured to transmit the output to at least one of an email server, a web server, a file server, and a mobile programmable device. The at least one processor may be configured to generate the output in response to at least one of receipt of the input, expiration of a periodic duration, an expiration of an aperiodic duration. The at least one processor may include a plurality of processors and the output may indicate whether at least one processor of the plurality of processes is operational. The output may include an indication of whether the user interface is operational.

The ambulatory medical device may further include a software component executable by the at least one processor and having a version, and the output may include an indication of the version. The ambulatory medical device may further include a network interface coupled to the at least one processor, and the at least one processor may be configured to transmit, via the network interface, information based on the data descriptive of the patient and the output may include an indication of when the information was last transmitted successfully. The output may include an indication of at least one operational issue and troubleshooting information associated with the at least one operational issue.

In the ambulatory medical device, the at least one sensor may include at least one electrocardiogram (ECG) sensor, the one or more operations may include monitoring cardiac function of the patient, and the output may include an indication of whether the at least one ECG sensor is in electrical communication with the patient's heart. The ambulatory medical device may further include a belt housing the at least one ECG sensor, and the output may include an indication of whether the belt has been subject to tensile forces in excess of a predetermined threshold value. The ambulatory medical device, may further include a battery having a remaining service life, and the output may include an indication of whether the remaining service life is less than a threshold value. The ambulatory medical device may further include at least one therapy electrode coupled to the at least one processor, the one or more operations may include treatment of cardiac arrhythmias, and the output may include an indication of whether the at least one therapy electrode is in electrical communication with the patient's heart. The ambulatory medical device may further comprise a charging circuit coupled to the battery and at least one capacitor, and the output may include an indication of whether the circuit is operational.

In another example, a method of providing status information for an ambulatory medical device is provided. The ambulatory medical device includes a plurality of subsystems. The method includes acts of identifying subsystem status information descriptive of an operational status of each subsystem of the plurality of subsystems and providing a device health report for the ambulatory medical device via the user interface, the device health report being based on the operational status of each subsystem.

In the method, the act of providing the device health report may include an act of providing operational status information descriptive of at least one of a monitor subsystem, an electrode subsystem, a battery subsystem, a base station subsystem, a garment subsystem, and a communications subsystem. In the method, the act of providing the operational status information may include an act of providing operational status information descriptive of at least one of a battery charger subsystem, a sensing electrode subsystem, a therapy electrode subsystem, a gel deployment subsystem, a sensor interface, a therapy delivery interface, a processing subsystem, and an energy storage and delivery subsystem. In the method, the act of identifying the subsystem status information may include an act of identifying a plurality of indications, each indication of the plurality of indications being associated with a subsystem of the plurality of subsystems and indicating whether the subsystem associated with the indication is in an operational state or a nonoperational state.

In one example, a non-transitory computer readable medium storing computer executable instructions to execute a method of providing status information for an ambulatory medical device is provided. The ambulatory medical device includes a plurality of subsystems. The computer executable instructions include instructions to identify subsystem status information descriptive of an operational status of each subsystem of the plurality of subsystems and to provide a device health report for the ambulatory medical device via the user interface, the device health report being based on the operational status of each subsystem.

The instructions to provide the device health report may include instructions to provide operational status information descriptive of at least one of a monitor subsystem, an electrode subsystem, a battery subsystem, a base station subsystem, a garment subsystem, and a communications subsystem. The instructions to provide the operational status information may include instructions to provide operational status information descriptive of at least one of a battery charger subsystem, a sensing electrode subsystem, a therapy electrode subsystem, a gel deployment subsystem, a sensor interface, a therapy delivery interface, a processing subsystem, and an energy storage and delivery subsystem. The instructions to identify the subsystem status information may include instructions to identify a plurality of indications, each indication of the plurality of indications being associated with a subsystem of the plurality of subsystems and indicating whether the subsystem associated with the indication is in an operational state or a nonoperational state.

Still other aspects, examples and advantages of these aspects and examples, are discussed in detail below. Moreover, it is to be understood that both the foregoing information and the following detailed description are merely illustrative examples of various aspects and features, and are intended to provide an overview or framework for understanding the nature and character of the claimed aspects and examples. Any example or feature disclosed herein may be combined with any other example or feature. References to different examples are not necessarily mutually exclusive and are intended to indicate that a particular feature, structure, or characteristic described in connection with the example may be included in at least one example. The appearances of such terms herein are not necessarily all referring to the same example.

DESCRIPTION OF DRAWINGS

Various aspects of at least one example are discussed below with reference to the accompanying figures, which are not intended to be drawn to scale. The figures are included to provide an illustration and a further understanding of the various aspects and examples, and are incorporated in and constitute a part of this specification, but are not intended as a definition of the limits of any particular example. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure.

FIG. 9 is a list of events that may trigger execution of tests in accordance with an example of the present disclosure.

FIG. 10 is a list of tests that a self-test component is configured to execute in accordance with an example of the present disclosure.

FIG. 11 is a cross-reference including associations between tests and subsystems in accordance with an example of the present disclosure.

DETAILED DESCRIPTION

Figure 1:
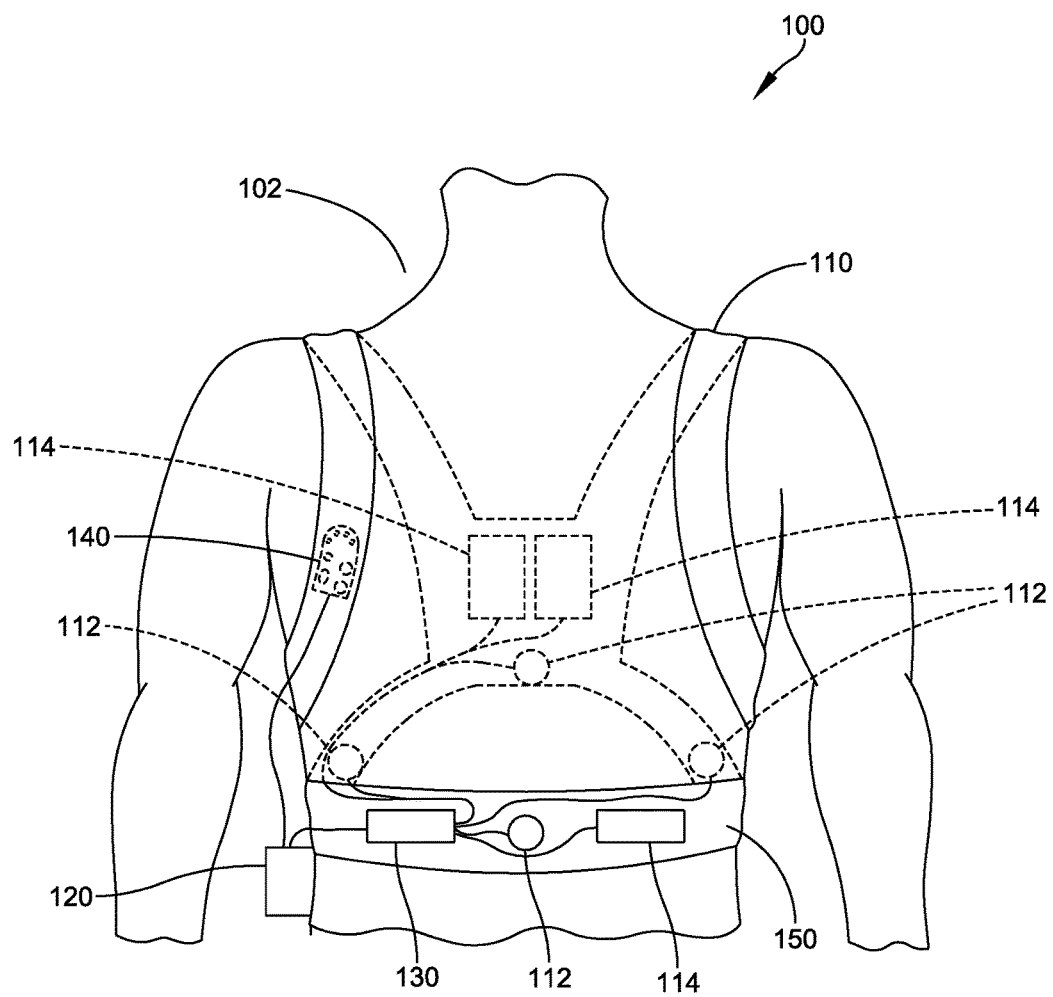
FIG. 1 is a schematic diagram of one example of a medical device in accordance with an example of the present disclosure.

Systems and processes disclosed herein include one or more reporting components configured to execute one or more reporting processes. These reporting processes provide interested persons with information regarding the operational status of a medical device monitoring a patient. In some examples, this information takes the form of a device health report that is provided by the medical device to the interested person on-demand and that may be accessed via a variety of channels.

In some examples, the reporting processes may also provide interested persons with details regarding the patient's activity. This patient activity information may include information descriptive of a variety of physical activities performed by the patient. For example, in some implementations, the reporting processes may capture patient activity information including device use information and/or patient health information including patient data, trends, statistics, and patient compliance information.

For instance, in some examples, a medical device includes a device health component that is configured to process requests to generate a device health report. When executing according to this configuration, the device health component receives requests to generate the device health report, queries a variety of data sources within the medical device to accumulate operational status information, and creates a device health report that presents the operational status information and/or summaries of this information within an organized and easily understood structure. The data sources queried by the device health component include data sources descriptive of a variety of subsystems of the medical device. These data sources may include data storage locations within a data storage device that are associated with one or more subsystems and/or predefined interfaces exposed by the subsystems. As such, when querying a data source, the device health component may read data stored at a storage location or programmatically call interfaces of other components.

In some examples, the subsystems identified in the device health report include one or more components of the medical device. Individual components may belong to a single subsystem or spanning multiple subsystems. In addition, these components may be hardware components and/or software components, and each of the components may have one or more identifiers that uniquely identify the component, and in some cases, associate the component with other components. Such identifiers may include, for example, model and/or version numbers.

In some examples, the operational status information received and stored by the device health component includes indications of whether or not particular subsystems of the medical device are in an operational state or a nonoperational state. In these examples, the device health component generates a device health report that is based on these indications.

The device health report, as generated by the device health component, may take a variety of forms. For example, the device health report may passively indicate operational status information or may actively notify one or more distinct devices of the operational status information. In addition, the device health report may include textual, graphical, and auditory elements. Furthermore, in some examples, the device health report may be reviewed via the medical device, a remote server in communication with the medial device, and/or another programmable device in communication with the medical device or the remote server.

In some examples, the medical device includes a patient activity component that is configured to process requests to generate patient activity reports. These patient activity reports may include device use reports and/or other patient information reports and are described in further detail below with reference to FIG. 19. In some implementations, the patient activity reports may be processed, presented, and distributed through similar mechanisms and channels as described herein for device health reports. For instance, the patient activity component may provide patient activity reports to the patient via a user interface.

Examples of the methods and systems discussed herein are not limited in application to the details of construction and the arrangement of components set forth in the following description or illustrated in the accompanying drawings. The methods and systems are capable of implementation in other examples and of being practiced or of being carried out in various ways. Examples of specific implementations are provided herein for illustrative purposes only and are not intended to be limiting. In particular, acts, components, elements and features discussed in connection with any one or more examples are not intended to be excluded from a similar role in any other examples.

Also, the phraseology and terminology used herein is for the purpose of description and should not be regarded as limiting. Any references to examples, components, elements or acts of the systems and methods herein referred to in the singular may also embrace examples including a plurality, and any references in plural to any example, component, element or act herein may also embrace examples including only a singularity. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. In addition, in the event of inconsistent usages of terms between this document and documents incorporated herein by reference, the term usage in the incorporated references is supplementary to that of this document; for irreconcilable inconsistencies, the term usage in this document controls.

Example Medical Devices

As disclosed herein, a medical device monitors a patient and, in some implementations, provides treatment to the patient based on the monitoring. For instance, in some examples, the medical device monitors one or more physiological parameters of the patient. More particularly, the medical device can be configured to monitor data digitized from one or more physiological signals acquired from a patient (e.g., ECG signals), heart beats, respiration, breath sounds, tissue fluids, lung fluids, lung sounds, chest movements, and/or cardiopulmonary anomalies, detect anomalies present in the digitized data, and determine whether the detected anomalies impair cardiac or pulmonary function. In various implementations, the medical device can be configured to monitor other patient parameters including but not limited to blood pressure, glucose levels, weight, blood oxygen, etc.

External medical devices as described herein may be in contrasted with internal devices, such as implantable medical devices. For example, the external medical devices as described herein may be capable of continuous, substantially continuous, long-term and/or extended monitoring of a patient or wear by, or attachment or connection to the patient. For instance, external medical devices as described herein may be capable of being used or worn by, or attached or connected to a patient, without substantial interruption for a predetermined period of time. In some examples, such external medical devices may be capable of being used or worn by, or attached or connected to a patient for example, up to hours or beyond (e.g., weeks, months, or even years).

Medical devices as disclosed herein can be configured to determine whether the patient may be experiencing a cardiac condition. For instance, the medical device can include a plurality of sensing electrodes that are disposed at one or more locations of the patient's body and configured to sense or acquire cardiac signals of the patient. Such medical devices can be used as cardiac monitors in certain cardiac monitoring applications, such as holter monitoring, mobile cardiac telemetry (MCT) and/or continuous event monitoring (CEM) applications. In some instances, the medical devices may carry out monitoring in periodic or aperiodic time intervals or times. For example, the monitoring during intervals or times can be triggered by a user action or another event. The one or more durations between the periodic or aperiodic intervals or times can be user-configurable.

In some implementations, the medical devices as described herein can be configured to monitor a patient presenting with syncope (e.g., by analyzing the patient's cardiac activity for aberrant patterns that can indicate abnormal physiological function). In some examples, aberrant patterns may occur prior to, during, or after the onset of syncope symptoms. For example, a short-term outpatient defibrillator can include a plurality of electrodes and/or an electrode assembly (patch) that can be adhesively attached to the patient's skin. The patient may replace the electrodes and/or patches as prescribed.

Example Wearable Medical Device

In some implementations, an external medical device capable of providing device health reports is an ambulatory device (e.g., a device that is capable of and designed for moving with the patient as the patient goes about his or her daily routine). In some examples, the external medical device can be configured as a wearable defibrillator, such as the LifeVest® wearable defibrillator available from ZOLL® Medical Corporation of Chelmsford, Mass.

FIG. 1 illustrates an example medical device 100 that is external, ambulatory, and wearable by the patient 102. The wearable medical device 100 includes a plurality of sensing electrodes 112 that can be disposed at various positions about the patient's body. The sensing electrodes 112 are electrically coupled to a medical device controller 120 through a connection pod 130. In some implementations, some of the components of the wearable medical device 100 are affixed to a garment 110 that can be worn on the patient's torso. For example, as shown in FIG. 1, the controller 120, at least some of the sensing electrodes 112, and, optionally, one or more therapy electrodes 114 can be mounted on a belt 150 worn by the patient. The sensing electrodes 112 and connection pod 130 can be assembled or integrated into the garment 110 as shown. The sensing electrodes 112 are configured to acquire signals descriptive of the cardiac function of the patient (e.g., by acquiring ECG signals of the patient). The connection pod 130 may include a signal processor configured to amplify, filter, and digitize these cardiac signals prior to transmitting the cardiac signals to the controller 120. In some implementations, a user interface module 140, which is optional as indicated by its rendering in dashed line form in FIG. 1, may be provided. Such a user interface module 140 may include a user interface, e.g., a display for displaying pertinent information to the patient or other interested person, a speaker for providing audible alarms, and/or one or more response buttons that may be used to communicate with the device in manners described herein. For example, the user interface module 140 may be used to provide feedback to or receive input from a user in addition to or instead of the user interface elements on the controller 120.

The wearable medical device 100 can also optionally include a plurality of therapy electrodes 114 that are electrically coupled to the controller 120 through the connection pod 130. The therapy electrodes 114 are configured to deliver one or more therapeutic defibrillating shocks to the body of the patient if the medical device 100 determines that such treatment is warranted. The connection pod 130 may include electronic circuitry and one or more sensors (e.g., a motion sensor, an accelerometer, etc.) that are configured to monitor patient activity.

Example Medical Device Controller

Figure 2A:
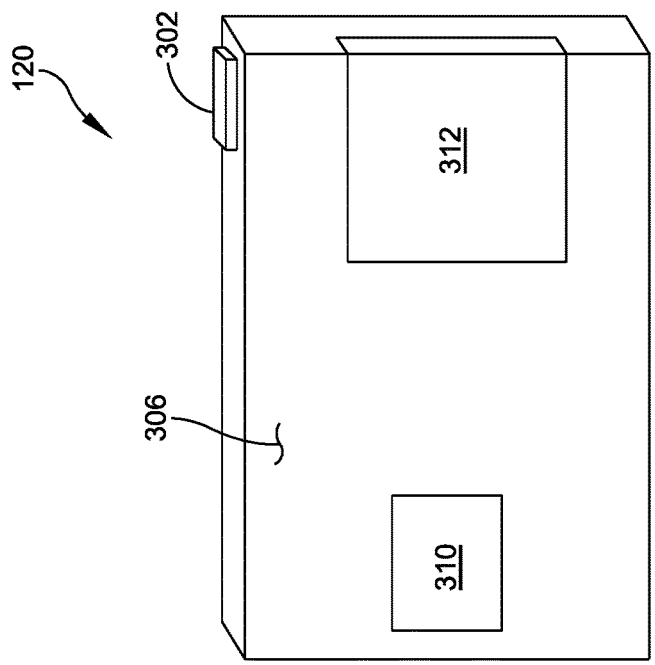
FIGS. 2A and 2B are schematic diagrams of a first side and a second side of one example of a medical device controller in accordance with an example of the present disclosure.
Figure 2B:
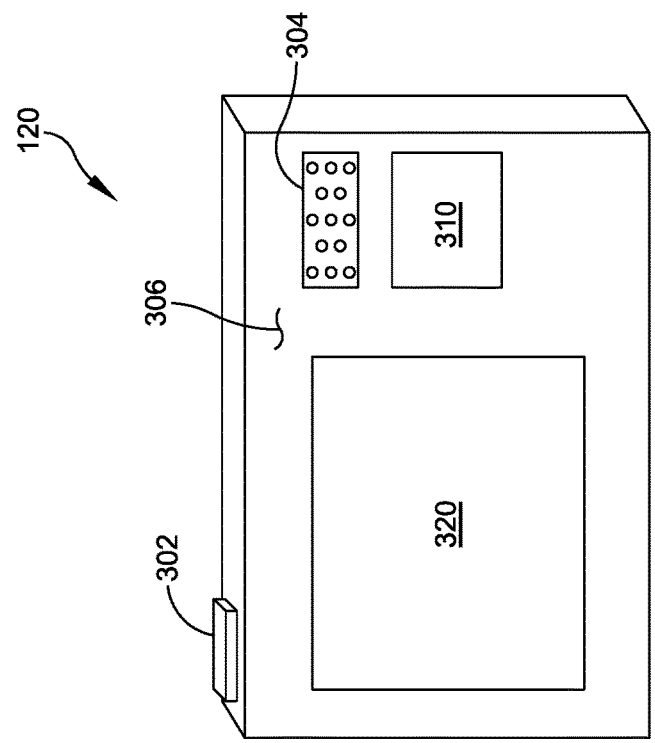

FIGS. 2A and 2B illustrate an example of the controller 120 including user interface elements (e.g., display 320) for providing the device health reports. It is appreciated that while display 320 is described herein as providing visual information to a user, other modes of providing information to the user can be implemented in addition to or instead of display 320, such as audio, tactile, and/or Braille output. The controller 120 may be powered by a rechargeable battery 312. The rechargeable battery 312 may be removable from a housing 306 of the controller 120 to enable a patient and/or caregiver to swap a depleted (or near depleted) battery 312 for a charged battery. The user interface elements can be configured to provide device health reports and related information to the patient, caregiver, and/or bystanders. For example, the display 320 can be implemented as a touch screen interactive user interface. Accordingly, the patient and/or caregiver can interact with the display 320 to control the medical device 100. The controller 120 also includes a speaker 304 for communicating information to the patient, caregiver, and/or the bystander. The controller 120 includes one or more response buttons 310. In some examples, when the controller 120 determines that the patient is experiencing cardiac arrhythmia, the speaker 304 can issue an audible alarm to alert the patient and bystanders to the patient's medical condition. In some examples, the controller 120 can instruct the patient to press one or both of the response buttons 310 to indicate that the patient is conscious, thereby instructing the medical device controller 120 to withhold the delivery of therapeutic defibrillating shocks. If the patient does not respond to an instruction from the controller 120, the medical device 100 may determine that the patient is unconscious and proceed with the treatment sequence, culminating in the delivery of one or more defibrillating shocks to the body of the patient. The controller 120 may further include a port 302 to removably connect sensing devices (e.g., sensing electrodes 112) and/or therapeutic devices (e.g., therapy electrodes 114) to the controller 120. In some examples, the sensing electrodes 112 include ECG sensing electrodes.

Figure 2D:
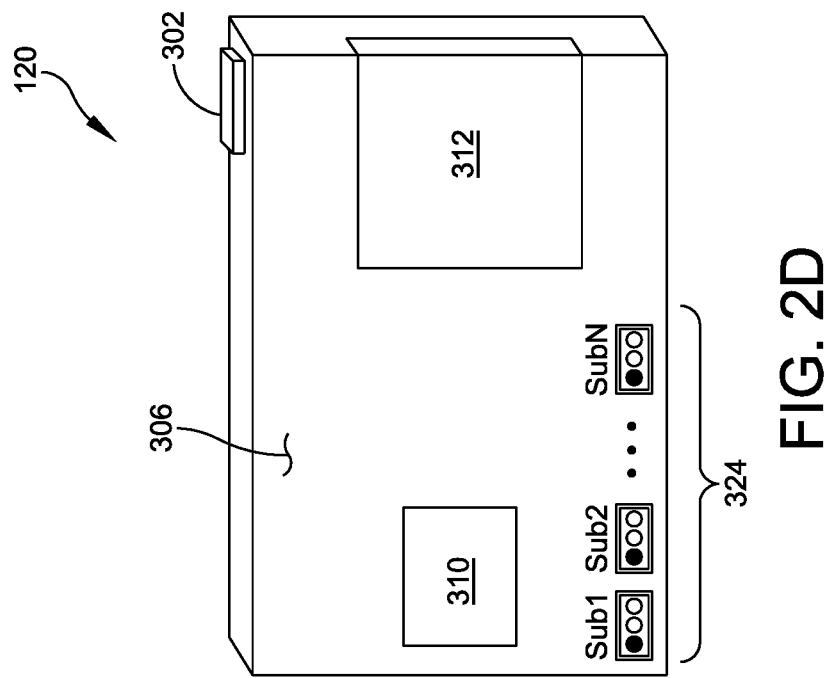
FIGS. 2C and 2D are schematic diagrams of a first side and a second side of another example of a medical device controller in accordance with an example of the present disclosure.
Figure 2C:
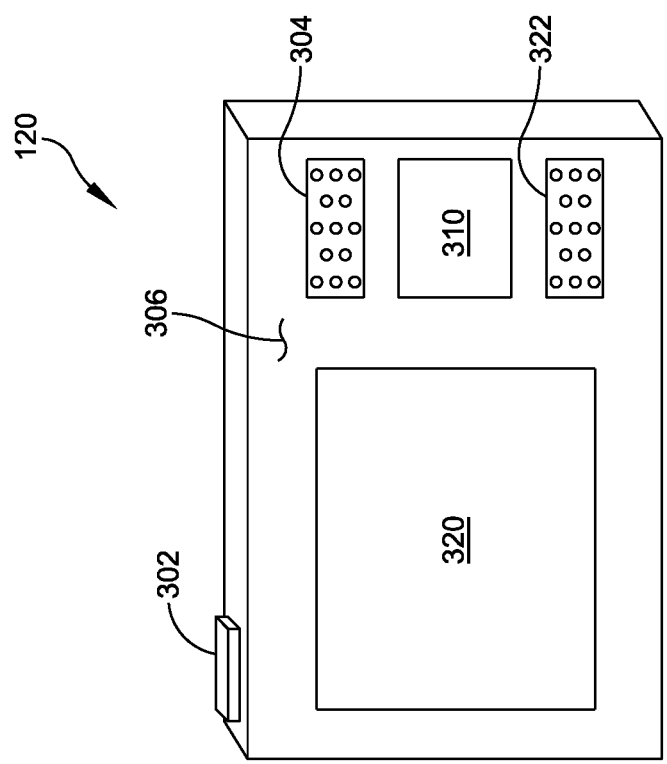

FIGS. 2C and 2D illustrate another example of the controller 120 including dedicated user interface elements (e.g., light emitting diodes (LEDs) 324 and speaker 322) for providing the device health reports. As described above, other types of visual elements may be used, e.g., display screens, or other visual indicators that may be caused to activate on receipt of an appropriate signal. The dedicated user interface elements can be configured to provide device health reports and related information to the patient, caregiver, and/or bystanders. For example, the LEDs 324 may be under control of a processor (e.g., processor 418, which is described further below with reference to FIG. 4) included within the controller. This processor 418 may be configured to control the LEDs to illuminate in a particular color (e.g., red to indicate a problem status that may need attention, and green to indicate operational status) that indicates the operational status of the subsystem. As shown in FIG. 2D, each of the LEDs 324 corresponds to a particular subsystem (e.g., subsystem 1, subsystem 2, . . . subsystem N) of the medical device 100. The controller 120 also includes a dedicated speaker 322 for communicating information to the patient, caregiver, and/or the bystander. The speaker 322 may emit sounds to form words and phrases of natural human language and/or sounds with various tonal qualities that are each distinctive of a subsystem and/or status of the subsystem. Individually, and in combination, the LEDs 324 and the speaker 322 provide fault-tolerance to the device health reporting functionality of the medical device 100.

Figure 3:
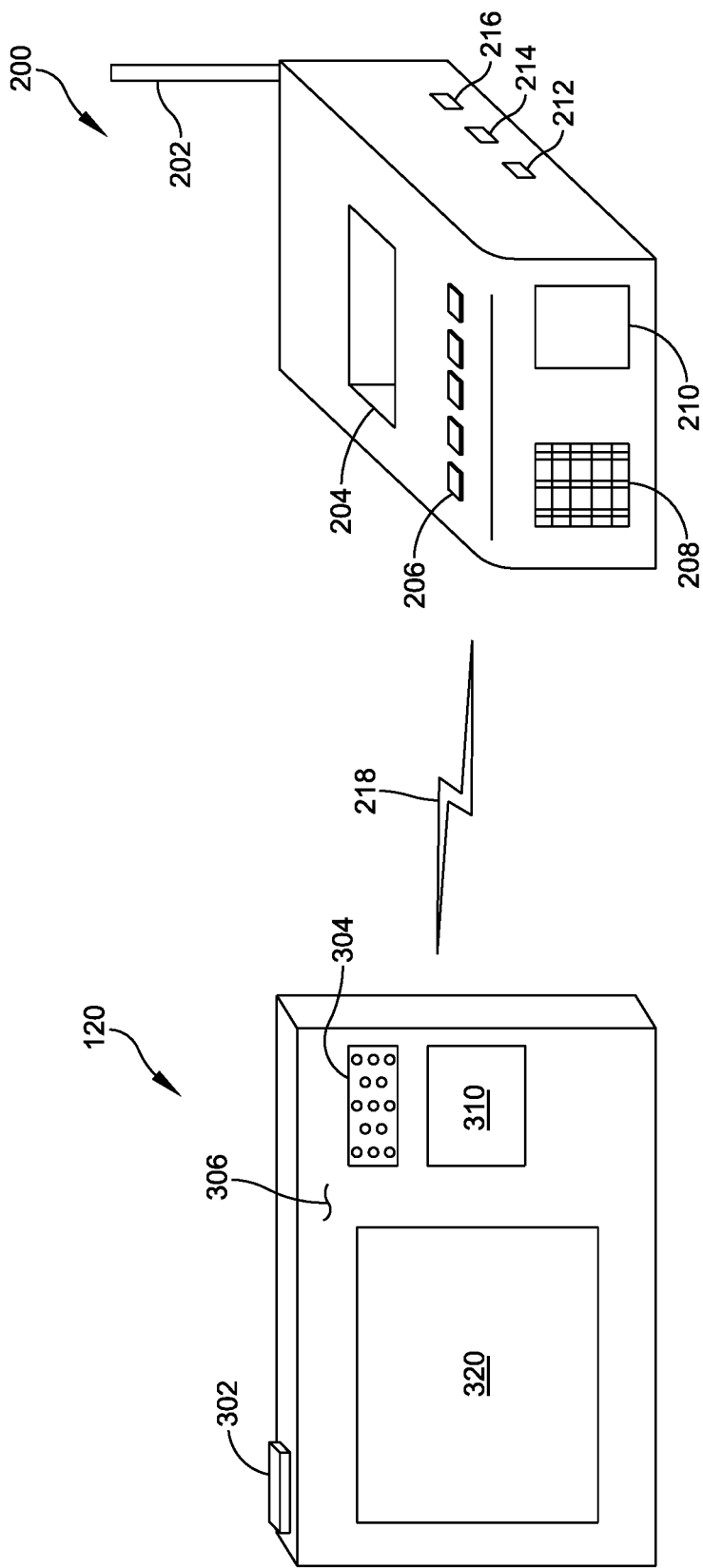
FIG. 3 is a schematic diagram of an example system including a medical device controller and a base station in accordance with an example of the present disclosure.

In some examples, the controller 120 may be in communication with a base station capable of performing a number of different functions. FIG. 3 illustrates the controller 120 in communication with a base station 200. As illustrated, the base station 200 includes an antenna 202; a battery charging bay 204; base station user interface element such as one or more buttons 206, a speaker 208, a display 210; and one or more communication interfaces 212, 214, and 216. The base station 200 communicates with the controller 120 via, for example, wireless communication connection 218, e.g., BLUETOOTH, Wireless USB, ZigBee, and Wireless Ethernet. The information received by the base station 200 may be communicated over a wired or wireless communication network shortly after it is received by the base station 200, or alternatively, may be stored in a memory of the base station 200 and communicated over the network at a later time. For example, information relating to the patient's medical condition and/or device status information over a period of time may be communicated by the base station 200 to a remote server through which a caregiver, such as a physician, may remotely monitor the patient's medical condition. In some examples, the base station 200 is capable of charging a rechargeable battery for the controller 120.

Figure 4:
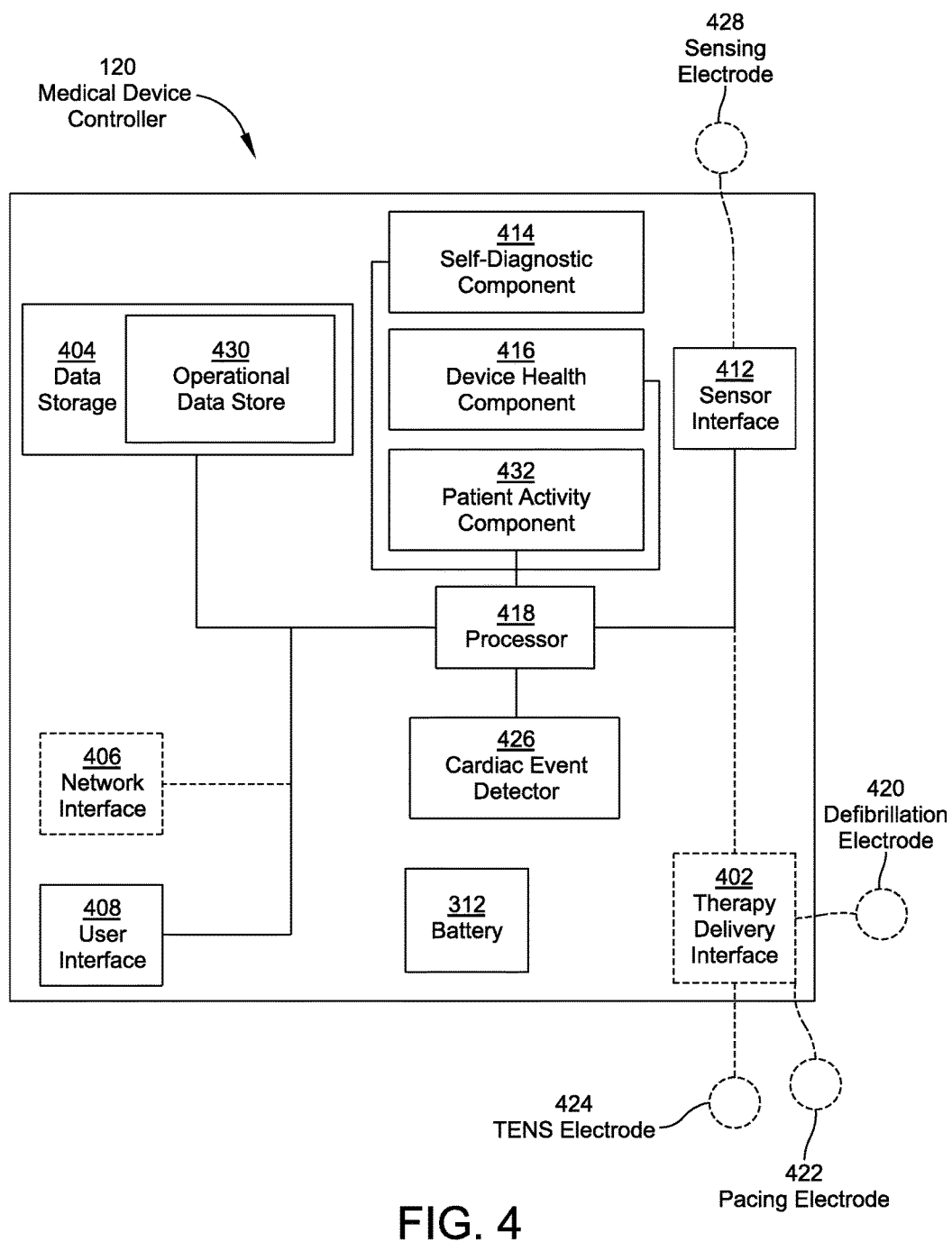
FIG. 4 is a block diagram of an example of a medical device controller in accordance with an example of the present disclosure.

FIG. 4 shows a schematic of an example of the controller 120 of FIGS. 1, 2A, 2B, and 3. The controller 120 includes at least one processor 418, self-diagnostic component 414, a device health component 416, a patient activity component 432, a sensor interface 412, an optional therapy delivery interface 402, data storage 404 (which may include operational data store 430), an optional network interface 406, a user interface 408, and the battery 312. The sensor interface 412 may be coupled to any one or combination of sensors to receive information indicative of patient parameters. For example, the sensor interface 412 may be coupled to one or more sensing devices including, for example, sensing electrodes 428. The therapy delivery interface 402 (if included) may be coupled to one or more electrodes that provide therapy to the patient including, for example, one or more defibrillation electrodes 420, pacing electrodes 422, and/or TENS electrodes 424. In some examples, the sensing electrodes 428 are included in the sensing electrode 112, and the defibrillation electrode 420, the pacing electrode 422, and/or the TENS electrode 424 are included in the therapy electrodes 114. The sensor interface 412 and the therapy delivery interface 402 may implement a variety of coupling and communication techniques for facilitating the exchange of data between the sensors and/or therapy delivery devices and the controller 120.

In some examples, the network interface 406 can facilitate the communication of information between the controller 120 and one or more other devices or entities over a communications network. For example, the network interface 406 may be configured to communicate with a server (e.g., a remote server) where a caregiver can access information related to the patient or with a base station (e.g., the base station 200) that is associated (e.g., paired) with the controller 120.

In some examples, the controller 120 includes a cardiac event detector 426 to monitor the cardiac activity of the patient and identify cardiac events experienced by the patient based on received cardiac signals.

In some examples, the user interface 408 includes one or more physical interface devices such as input devices, output devices, and combination input/output devices and a software stack configured to drive operation of the devices. These user interface elements may render visual, audio, and/or tactile content, including content relating to the device health status. For instance, in some examples, the user interface 408 includes a microphone, the speaker 304, the display 320, and the response buttons 310. Thus, the user interface 408 may receive input or provide output, thereby enabling a user to interface with the controller 120.

In some implementations, the processor 418 includes one or more processors that each can perform a series of instructions that result in manipulated data and/or control the operation of the other components of the controller 120. In some implementations, when executing a specific software process as provided herein (e.g., FIGS. 5 and 6), the processor 418 is configured to make specific logic-based determinations based on input data received, and further capable of providing one or more outputs that can be used to control or otherwise inform subsequent processing to be carried out by the processor 418 and/or other processors or circuitry with which processor 418 is communicatively coupled. Thus, the processor 418 reacts to specific input stimulus in a specific way and generates a corresponding output based on that input stimulus. In this sense, the structure of processor 418 according to one example is defined by the flow charts shown in FIGS. 5 and 6. In some example cases, the processor 418 proceeds through a sequence of logical transitions in which various internal register states and/or other bit cell states internal or external to the processor 418 may be set to logic high or logic low. This specific sequence of logic transitions is determined by the state of electrical input signals to the processor 418 and a special-purpose structure is effectively assumed by the processor 418 when executing each software instruction of the software process shown in FIGS. 5 and 6. Specifically, those instructions anticipate the various stimulus to be received and change the implicated memory states accordingly. In this way, the processor 418 may generate and store or otherwise provide useful output signals. It is appreciated that the processor 418, during execution of a software process is capable of processing specific input signals and rendering specific output signals based on the one or more logic operations performed during execution of each software instruction. As referred to herein, the processor 418 is configured to execute a function where software is stored in a data store coupled to the processor 418 that is configured to cause the processor 418 to proceed through a sequence of various logic decisions that result in the function being executed.

In various implementations, the controller 120 implements an embedded operating system that supplies file system and networking support. In one example, the controller 120 includes software features that provide relational database functionality, touch screen display drivers, audio generation, BLUETOOTH wireless networking, networking security and firewalling, a lightweight web server and data encryption services.

Example Patient Activity Component

The patient activity component 432 illustrated in FIG. 4 is configured to generate one or more patient activity reports and provide the one or more patient activity reports to a user interface accessible by a user, such as the patient 102, a caregiver, or another person. In some examples, this user interface includes the user interface 408, which may include the display 320. When executing according to its configuration, the device health component 416 queries one or more data sources for patient activity information descriptive of the patient's use of the medical device or other physical activities performed by the patient and presents one or more indications of the patient activities via a user interface accessible to a user. The patient activity component 432 may execute these and other processes in a periodic, aperiodic, or on-demand (event driven) manner.

The data sources queried by the patient activity component 432 may vary between examples. For instance, these data sources may include one of more patient sensors such as accelerometers, gyroscopes, and other patient movement sensors. In some cases, the data sources may also collect and/or store information about a use of the medical device by the patient, and also track patient statistics and/or compliance information as described below. For example, this information may include patient information (e.g., patient data, statistics, and trends) while the patient is wearing the device, such as an amount of time of device wear, steps taken by the patient while wearing the device, steps taken by the patient while wearing the device during a prescribed activity (such as a six minute walk test), hours spent by the patient in a reclined state, moving state, lying state, and upright state, among others.

The patient activity component 432 may present device use information in a summary form. For example, the patient (or other user) may be able to view a number of steps taken by the patient during a particular time period (e.g., "You have taken 2349 steps today"). For example, the patient's time of use or wear may be presented to the patient via the device user interface (e.g., "You wear your device for an average of 18.6 hours a day"). Other modes of viewing the data are possible. For example, the patient may be able to view his or her data trends over a period of time as described below.

In some examples, patient activity component 432 may present user interface elements that enable the patient to drill down into the device use data to view details of the information. For instance, the patient may be able to view a detailed step count over a period of time (e.g., a month) in the form of a bar chart showing a number of steps taken by the patient during each day of device wear in a past period including days, week or month. In another example, the patient may be able to view his or her daily time of use or wear of the device in the form of a bar chart showing a number of hours the patient wears the device each day of a period including preceding days, week, or month.

Example Self-Diagnostic Component

Figure 8:
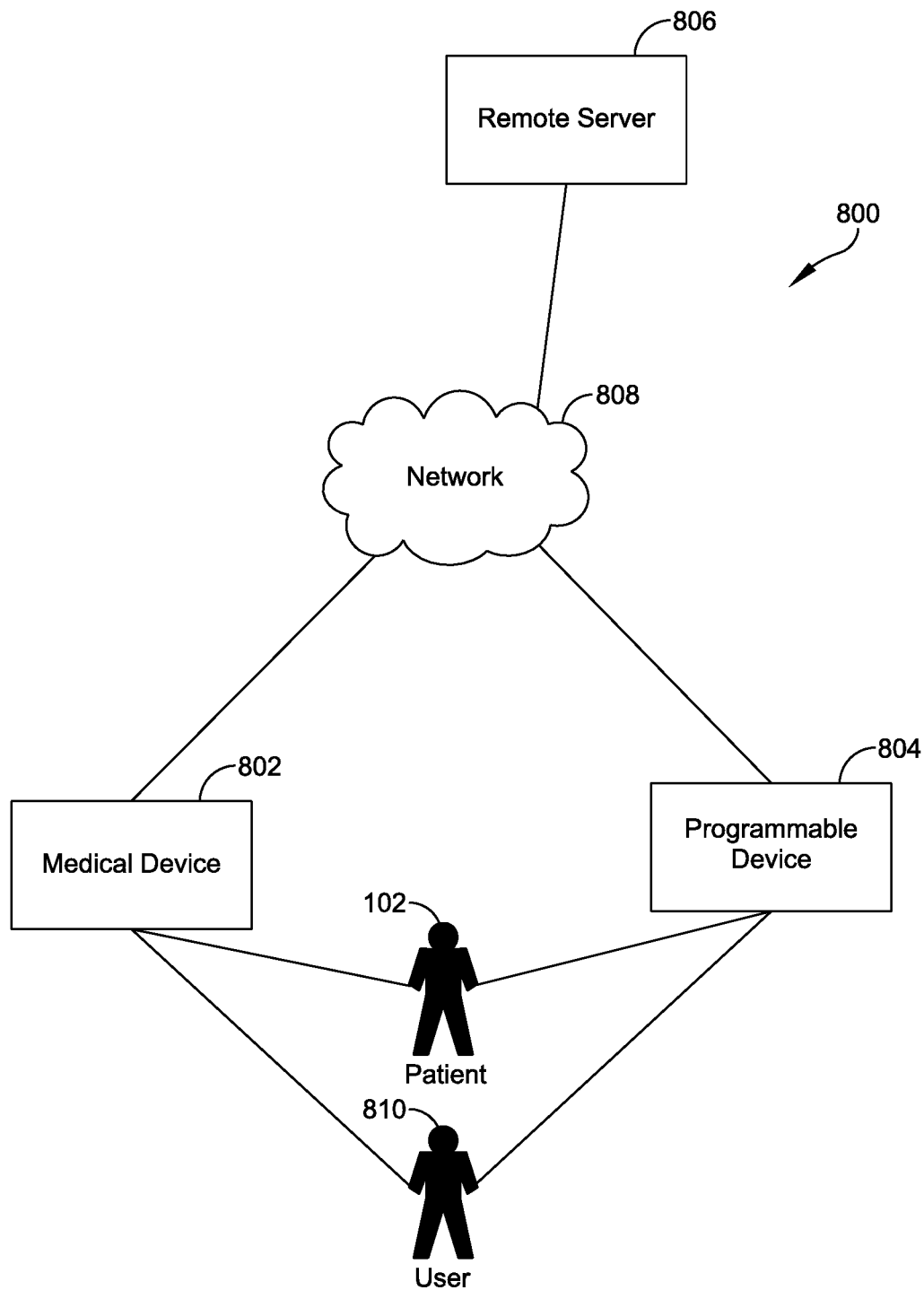
FIG. 8 is a block diagram of an example of a report distribution system in accordance with an example of the present disclosure.

The self-diagnostic component 414 illustrated in FIG. 4 is configured to execute one or more tests that evaluate the operational integrity of various subsystems of a medical device including the controller 120. Tests as described herein may be hardware or software tests, or a combination of both. For example, tests may be configured to assess the functioning status of critical components of the system. Some tests may be deemed optional and suspended when the device is operating in, for example, low power or distressed mode. For example, a low power or distressed mode may include a state of the device and/or system where a current battery capacity is below a certain threshold (e.g., less than 20% of battery capacity). Other thresholds below which the device and/or system may be automatically placed in low power or distressed mode are possible, including 40%, 30%, 25%, or 15% of battery capacity. In some cases, instead of automatically placing the device in such mode(s), the device may prompt the patient regarding the status of the device, and allow the patient to manually enable the mode(s). When executing according to its configuration, the self-diagnostic component 414 executes tests periodically, aperiodically, or in response to an event. FIG. 9 lists events that may cause the self-diagnostic component 414 to execute a test. In addition to the events listed in FIG. 9, an event of receiving a request to execute a test from another component of the controller 120 (e.g., the user interface component 408, the device health component 416, etc.), another component of the medical device, or a remote server (as illustrated in FIG. 8 below) may cause the self-diagnostic component 414 to execute one or more tests. In some examples, the self-diagnostic component 414 is configured to communicate a request to generate a device health report to the health component 416 in response to detecting an anomalous operational status via one or more tests.

The tests that the self-diagnostic component 414 is configured to execute vary between examples and depend on the subsystems and components present in the medical device. FIG. 10 lists some examples of tests that the self-diagnostic component 414 is configured to execute according to at least one example. More details regarding the events identified and tests executed by the self-diagnostic component 414 are described in U.S. Patent Application Ser. No. 62/135,910, titled "Systems and Methods for Testing a Medical Device," filed Mar. 20, 2015, which is attached hereto as Appendix A and which is hereby incorporated herein by reference in its entirety.

Example Device Health Component

The device health component 416 illustrated in FIG. 4 is configured to generate a device health report and provide the device health report to a user interface accessible by a user, such as the patient 102, a caregiver, or another person. In some examples, this user interface includes the user interface 408, which may include the display 320. As described further below, when executing according to its configuration, the device health component 416 queries one or more data sources for operational status information descriptive of one or more subsystems, interprets the operational status information acquired via the queries to infer a conclusion regarding the ability of the one or more subsystems to operate according to specification, and presents one or more indications of the inferred conclusions to a user interface accessible to a user. The device health component 416 may execute these and other processes in a periodic, aperiodic, or on-demand (event driven) manner.

The data sources queried by the device health component 416 may vary between examples. For instance, these data sources may include data storage locations at which operational status information is stored and/or interface calls (e.g., of one or more application program interfaces or "APIs") that return operational status information. In at least one example, the device health component 416 issues an API call to the self-diagnostic component 414 to acquire operational status information. The data sources may vary according to the subsystems that are included in the medical device. In addition, some or all of these data sources may be populated as a byproduct of normal medical device operation, in response to a request issued by the device health component 416, and/or as a result of tests executed by the self-diagnostic component 414. In the case of device use information, the device subsystems may include one of more patient sensors including accelerometers, gyroscopes, and other patient movement sensors.

In some examples, to identify the one or more data sources to query, the device health component 416 is configured to access one or more data structures that identify data sources. These data structures may be stored in the operational data store 430, along with previously generated device health reports and the operational status information used to generate those reports. In some examples, the one or more data structures that identify the data sources combine to form a cross-reference that associates the data sources with one or more subsystems. For example, the cross-reference may store identifiers of data sources in association with identifiers of the subsystems. FIG. 11 illustrates one such cross-reference, the cross-reference 1100.

The cross-reference 1100 associates multiple data sources (e.g., one for each test executable by the self-diagnostic component 414) with subsystems of a medical device. More specifically, as shown in FIG. 11, the cross-reference 1100 associates data sources with a monitor subsystem, an electrode subsystem, a battery subsystem, a base station subsystem, a garment subsystem, and a communications subsystem. The components included in each of the subsystems may vary between examples. However, the monitor subsystem generally includes the controller 120 and its components, as illustrated in FIGS. 2A, 2B, 3, and 4.

In some examples, the monitor subsystem includes a processing subsystem that includes the processor 418 and the data storage 404. The electrode subsystem generally includes the therapy electrodes 114, the sensing electrodes 112, the connection pod 130, and associated wires and cables, as illustrated in FIG. 1. The battery subsystem generally includes the battery 312, as illustrated in FIGS. 2B, and 4. The base station subsystem generally includes the base station 200 and its components, as illustrated in FIG. 2. In some examples, the base station subsystem includes a battery charger subsystem that includes a battery charging circuit. The garment subsystem generally includes the garment 110 and its components, as illustrated in FIG. 1. In some examples, the garment subsystem includes a shirt and/or a belt. Both the shirt and the belt may be fabricated using elastic materials to improve the fit of the garment to the patient's body.

In some examples, the electrode subsystem includes a gel deployment subsystem, sensing electrode subsystem, a therapy electrode subsystem, and a signal acquisition and processing subsystem, which includes the connection pod 130. In at least one of these examples, the gel deployment subsystem is configured to dispense impedance reducing gel on the patient's body. In some examples, the electrode subsystem includes the garment subsystem. In some examples, the electrode subsystem comprises fasteners configured to attach the sensing electrode subsystem and/or the therapy electrode subsystem to the patient (e.g., one or more areas of the patient's body, such as the upper torso region) or to a garment worn by the patient. These fasteners may include mechanical snap connectors, adhesive tape, and/or an adhesive layer configured to couple an electrode assembly housing either a therapy electrode or a sensing electrode to the patient's body or a garment worn by the patient. In some examples, the monitor subsystem, the electrode subsystem, the garment subsystem, and the battery subsystem include an energy storage and delivery subsystem that includes the battery 312, the therapy delivery interface 402, and the therapy electrodes 114. The communications subsystem generally includes the network interface 406 and/or communication components housed in the base station.

As illustrated by FIG. 11, in some examples, the tests associated with the monitor subsystem include tests that validate the operational integrity of processing elements (e.g., the processor 418), memory elements (e.g., the data storage 404), user interface elements (e.g., the user interface 408), and therapy delivery deliver elements (e.g., the therapy delivery interface 402). For instance, the tests associated with the monitor subsystem may check the capacitor charging circuit to verify the capacitors can be charged appropriately for delivery of one or more therapeutic defibrillating and/or pacing pulses.

In some examples, the tests associated with the electrode subsystem include tests that validate the operational integrity of sensing electrodes (e.g., the sensing electrodes 112), therapy electrodes (e.g., the therapy electrodes 114), the gel deployment subsystem, and/or a vibration box (e.g., part of the user interface 408) located in a connection pod (e.g., the connection pod 130). For instance, the tests associated with the electrode subsystem may check to ensure that the electrode cables have not experienced tensile forces in excess of a threshold value and that the signal strength and impedance measured at the electrodes in the electrode subsystem are within one or more acceptable ranges.

For example, a combination of software and hardware tests may include mechanisms that simulate an input and read one or more resulting outputs. The outputs may then be compared to a set of known good values and it is then determined if a component within the one or more subsystems (e.g., the electrode subsystem) is malfunctioning or requires calibration. For example, critical components on the electrode subsystem may include accelerometer, gyro, heart sounds sensor, and analog front end for receiving ECG and/or electrical signals from the patient. The software and/or hardware test circuitry may include signal generators for generating test stimulus signals.

Electrode Subsystem Power Tests

The electrode subsystem power test measures all power supplies of the electrode subsystem to ensure proper function of voltage regulators and other circuitry.

Electrode Subsystem Current Tests

The electrode subsystem current test measures the current consumption of the electrode subsystem, including, in some implementations, peak to peak fluctuation of current consumption.

Gel Deployment Subsystem Tests

In an implementation, the gel deployment subsystem test verifies the status of the gel in the belt, checks the integrity of the gel deployment circuitry with a test signal, and/or measures resulting signals for the duration of the test.

Electrode Falloff Tests

The falloff test cycles the electrodes on and off with relays and measures the falloff status reported by the signal acquisition circuitry. The test can be configured to cycle through one or more falloff possibilities in which one electrode is off, for each electrode. Then the test can cycle through the falloff possibilities in which only one electrode is on, for each electrode.

Sensors Tests

The accelerometer test can be configured to measure each axis of an accelerometer individually to determine if the MEMS accelerometer is functioning properly. The heart sounds sensor and the gyroscope can be tested in a similar manner.

Front End Tests

The analog front end can be tested to ensure that, e.g., amplifiers and one or more analog to digital converters (ADCs) are working properly. For example, a function generator can be used to generate input signals. The output can be analyzed with a fast Fourier transform running analysis to verify its performance at specific frequencies.

Tensile Strength Tests

In an example implementation, tensile forces in excess of one or more thresholds in the electrode subsystem may be detected as follows. For example, one or more devices for indicating forces on belt components such as belt wiring and related structures may be disposed at or proximate to one or more points of attachment. For example, such points of attachment may include where one or more cables in the electrode subsystem connect to each therapy electrode 114, sensing electrode 112, and/or the connection pod 130. Such devices may include strain gauges that are configured to monitor one or more tensile stresses on a jacket of a cable in the electrode subsystem and communicate stress information to a processor (e.g., processor 418). In addition or alternatively, the strain gauge may be configured to monitor tensile stress experienced by a cable at a point of attachment. For example, a cable jacket may be monitored to detect if the jacket displaces with respect to a conductor of the cable in excess of a threshold amount. In implementations, such a threshold may be 2 mm. In another example, the threshold may be less than 2 mm, or greater than 2 mm. In a further example, a cable at a point of attachment may be monitored to detect if the cable experiences a force greater than a predetermined threshold (e.g., 25 lbs.) for a predetermined amount of time (e.g., greater than 15 seconds). In another example, a cable at a point of attachment may be monitored to detect brief or instantaneous forces greater than a predetermined threshold (e.g., 50 lbs.). For example, such thresholds may be a user-configurable input (e.g., configurable by a service technician via a service user interface of the medical device) or implemented as a device parameter within a tensile force monitoring module executed by the processor 418. In one example, such a tensile force monitoring module can execute one or more of the following actions: one or more values representing tensile forces on a cable at a point or attachment may be received, the one or more values may be stored in a buffer variable, the one or more values may be compared with predetermined thresholds to determine whether any of the one or more values transgresses thresholds in a predetermined manner. For example, such predetermined manner may take into account factors such as a number of times that threshold transgressions occur, an amount by which the values exceed the thresholds, and an amount of time of threshold transgressions. If the monitoring module determines that the tensile forces exceed the thresholds in the predetermined manner, a flag may be declared and stored for access by, e.g., the self-diagnostic component 414, or the device health component 416 for reporting to an interested person.

In some examples, the tests associated with the battery subsystem include tests that validate the operational integrity of a battery (e.g., the battery 312). For instance, the tests associated with the battery subsystem may check the remaining battery runtime, the ability of the battery to hold a charge, and the remaining battery service life.

In some examples, the tests associated with the base station subsystem include tests that validate the operational integrity of battery charging components included in base station (e.g., the base station 200). For instance, the tests associated with the base station subsystem may verify the charging circuit can provide appropriate power to charge batteries connected to the charging circuit (e.g., by being inserted into the battery charging bay 204).

In some examples, the tests associated with the garment subsystem include tests that validate the operational integrity of sensing electrodes (e.g., 112) and therapy electrodes (e.g., 114) included in a garment (e.g., the garment 110). For instance, the tests associated with the garment subsystem may check to ensure that the impedance measured at the electrodes in the garment is within an acceptable range.

As shown in FIG. 11, the cross-reference 1100 includes an association between a "Network Connectivity Test" and the communication subsystem. In some examples, the self-diagnostic component 414 executes the Network Connectivity Test to determine whether the network interface 406 is operational. Some examples of the Network Connectivity Test execute a ping command (or some other connection testing component) to determine whether the network interface 406 is in data communication with a remote device. The Network Connectivity Test may also check to determine whether file communication activities (e.g. uploads and/or downloads) meet a currency requirement. The currency requirement may specify a predefined relationship between the current time and a time when the communication activities where last completed successfully. The predefined relationship may require, for example, that the communication activities be successfully completed within 24 hours of the current time, although other relationships ranging from 1 hour to 1 week may be configured.

The examples disclosed herein are limited to the subsystems and associated data sources (e.g., tests) described above. For instance, in some examples, the communication subsystem is incorporated into the base station subsystem. Thus, example may rearrange and/or omit the subsystems described above with departing from the scope of the present disclosure.

Additional examples of processes that the device health component 416 is configured to execute are described below with reference to FIGS. 5 and 6. In addition, FIG. 7 illustrates an example device health report that is generated via execution of these processes.

Example Report Processes

As described above, some examples execute one or more reporting processes. FIG. 5 illustrates one of these processes, an input handling process 500. As shown, the input handling process 500 is executed by a reporting component (e.g., the device health component 416 and/or the patient activity component 432) of a medical device. The medical device including the reporting component may be any medical device described herein.

The input handling process 500 starts in act 502, where the reporting component monitors a user interface for interactions with a user that indicate a request for a report. This user interface may be integral to the medical device (e.g., the user interface 408) or distinct and remote from, but in communication, with the medical device (e.g., via the network interface 406). The user may be a patient (e.g., the patient 102), a caregiver, or another person. Examples of interactions between the user and the user interface that may be inferred by the reporting component as a request to generate and provide a report include: selection of a user interface element such as a physical button (e.g., either or both of the response buttons 310), a virtual button displayed on a touch screen (e.g. the display 320), etc.; multiple actuations of a user interface element (e.g., 5 actuations within 10 seconds or some other predetermined, configurable period of time); and physical movement (shaking, tapping, gesturing, etc.) of at least a portion of the medical device (e.g., the controller 120). In at one example, selection of a button that indicates the medical device is functioning properly is inferred by the device health component as a request to generate and provide the device health report. It is appreciated that, in this example, the button that indicates the medical device is functioning properly is separate and distinct from the device health report described herein.

In some examples, the user interface presents one or more selectable elements, such as the virtual button described above, that may be subject to the interactions. For instance, in some examples, the device health component presents selectable elements via the user interface in response to an event, such as the medical device detecting an anomalous operational status of a component. In these examples, the user interface may present information regarding the anomalous operational status and may display a "help" button that, when actuated, is inferred by the device health component as a request to generate and provide the device health report.

Figure 16:
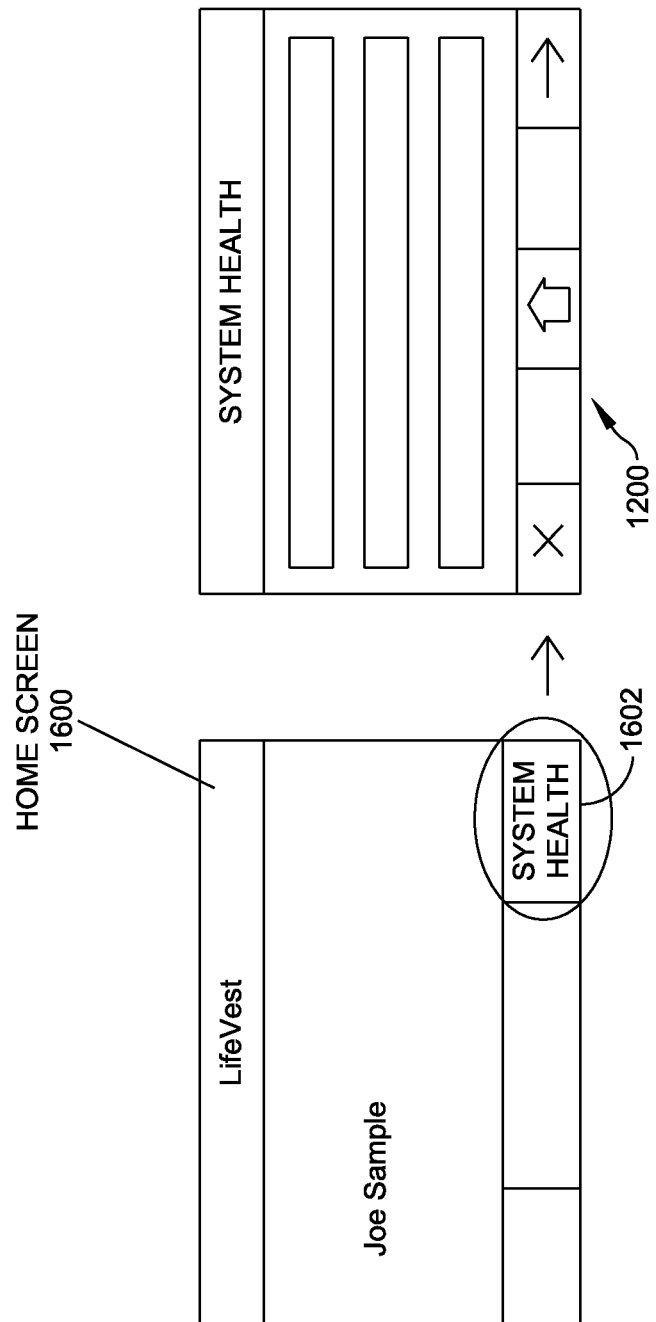
FIG. 16 is an illustration of user interface elements enabling access to a device health report in accordance with an example of the present disclosure.
Figure 17:
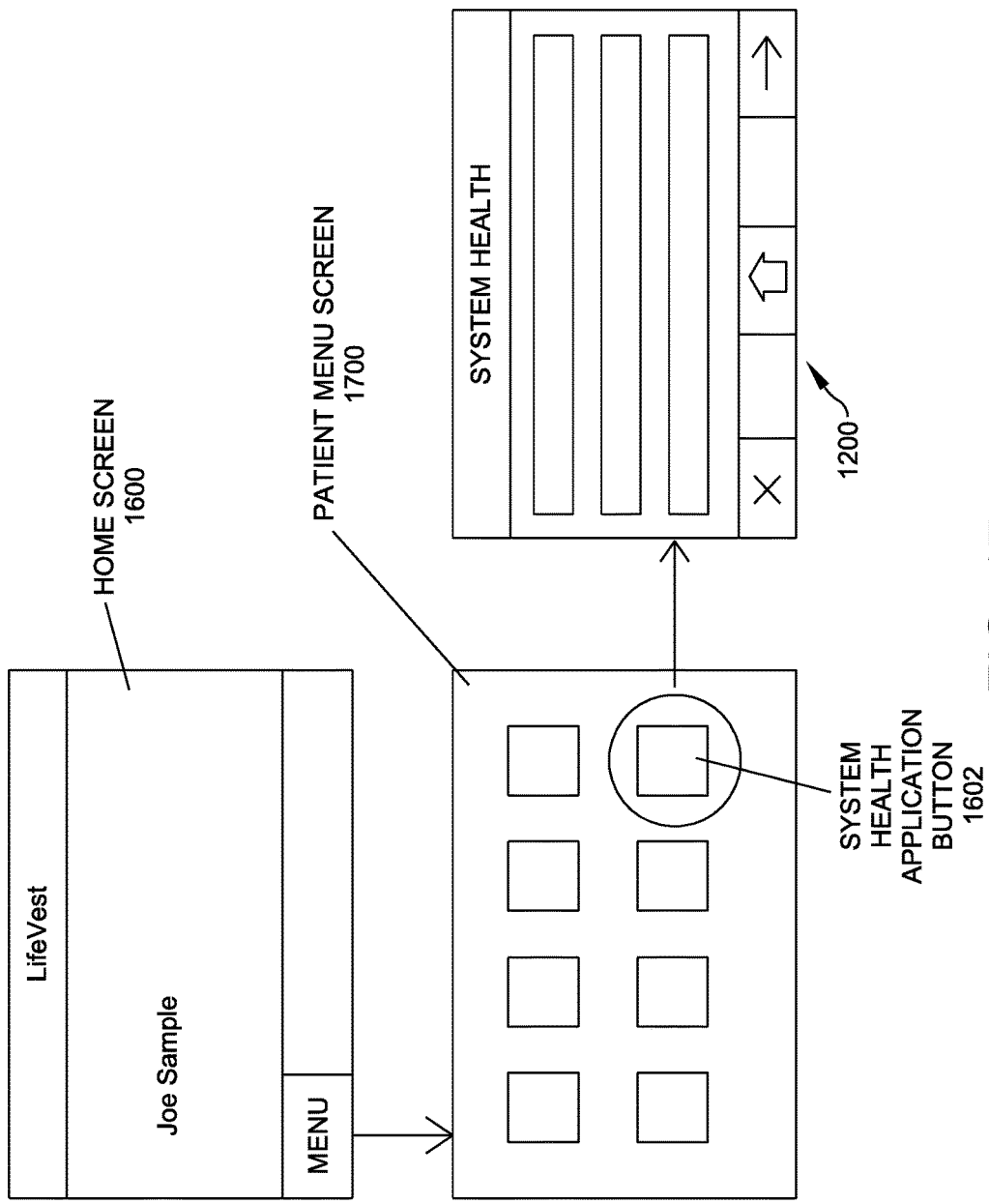
FIG. 17 is an illustration of user interface elements enabling access to a device health report in accordance with an example of the present disclosure.
Figure 18:
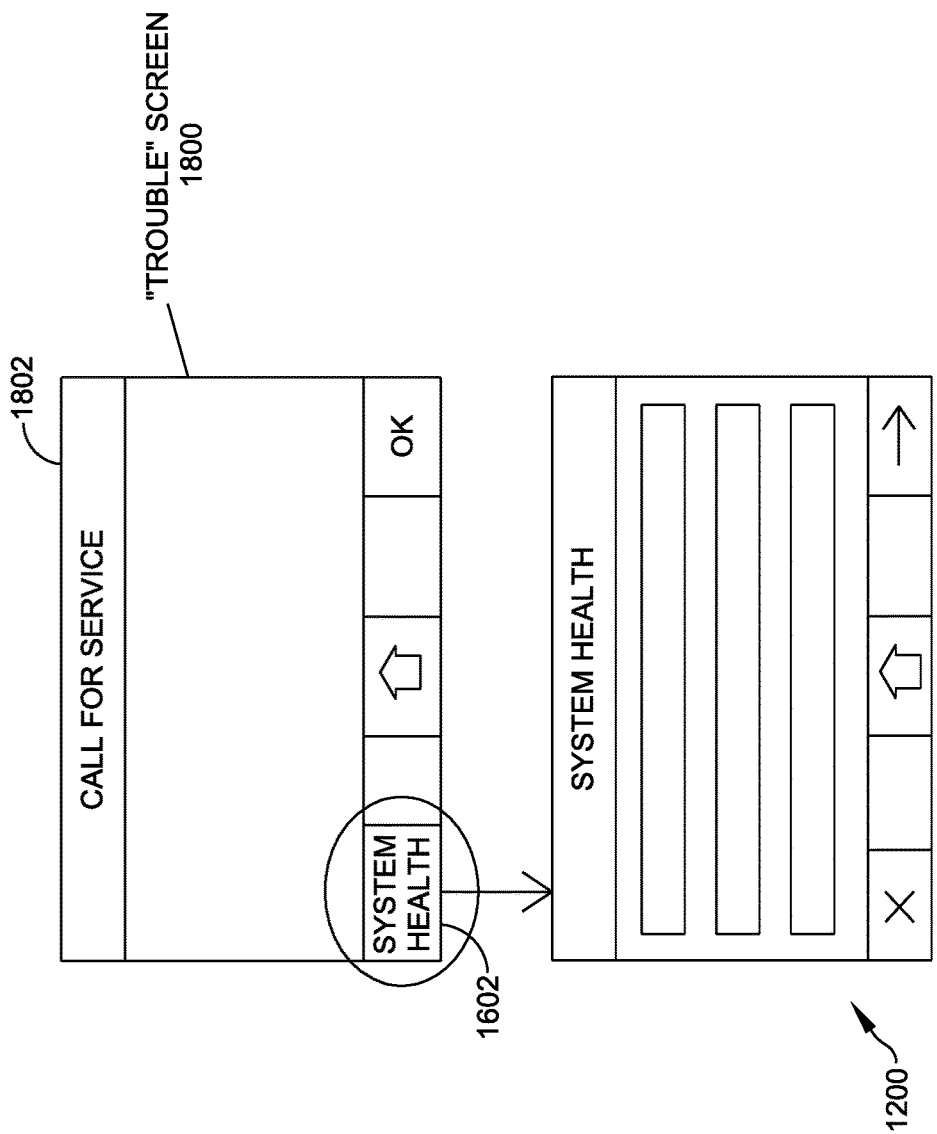
FIG. 18 is an illustration of user interface elements enabling access to a device health report in accordance with an example of the present disclosure.

FIGS. 16-18 illustrate various examples of one or more selectable elements that the device health component may provide via a user interface in some implementations. As shown, FIG. 16 includes a home screen 1600 and a system health report 1200. In some examples, the home screen 1600 is a top level menu that is presented to the user during normal medical device operation. The home screen 1600 includes a system health report button 1602 selectable to cause the device health component to display the system health report 1200, which is described further below with reference to FIG. 12.

As shown, FIG. 17 includes a patient menu screen 1700, a home screen 1600, and a system health report 1200. The patient menu screen 1700 allows the patient to access and change various options, such as to manually send data, change the speak options, view system information, connect to a specific charger, and set the medical device to airplane mode. The patient menu screen 1700 includes a system health report button 1602 selectable to cause the device health component to display the system health report 1200.

As shown, FIG. 18 includes a trouble screen 1800 and a system health report 1200. The trouble screen 1800 is displayed by the medical device (e.g., by the self-diagnostic component 414) when the medical device detects an anomalous operational status of a subsystem. The trouble screen 1800 includes a system health report button 1602 selectable to cause the device health component to display the system health report 1200. The trouble screen 1800 also includes a call for service button 1802 selectable to cause the device health component to establish an interactive communication session with a support representative. This interactive communication session may include a chat session, video conference, and/or telephone call. In some examples, the interactive communication session begins by presenting the most recently generated device health status report to the support representative and/or user. Further, the user interface through which the interactive communication session is executed may be included in the medical device providing the trouble screen 1800 or a programmable device in communication with the medical device and accessible by the user (e.g., a computer system, smart phone, etc.).

In some examples, the information presented in the trouble screen 1800 varies depending on a severity of the anomalous operational status reported by the trouble screen 1800. For instance, in one example, anomalous operational statuses are categorized into two groups (e.g., Group One and Group Two) based on severity. When the medical device is in a Group One status, the patient can continue to use the medical device. When the medical device is in a Group Two status, the patient must discontinue use of the medical device. When displaying information about a Group One status, which includes less severe anomalous operational statuses, the trouble screen 1800 includes specific information about the detected anomaly and its most likely cause(s), along with a message that the patient should contact a support representative but should continue to use the medical device. Group One statuses can be "reset" by manipulating the medical device in some predetermined manner (e.g., pressing an acknowledgment button to acknowledge the event, rebooting the medical device by pressing a reset button, turning a power switch on and off, or removing and reinserting the battery, etc.). When displaying information about a Group Two status, which includes more severe anomalous operational statuses, the trouble screen 1800 includes specific information about the detected anomaly and its most likely cause(s), along with a message that the patient should immediately contact a support representative. Group Two statuses cannot be reset, as the device has been deemed non-operational due to failure of a specific test. In addition, in some implementations, the trouble screen 1800 displays additional information when reporting an anomalous operational status belonging to Group Two. This additional information may include directions to be followed immediately, such as to replace a component of the medical device that is serviceable by the patient and to remove the device from the patient.

Figure 19:
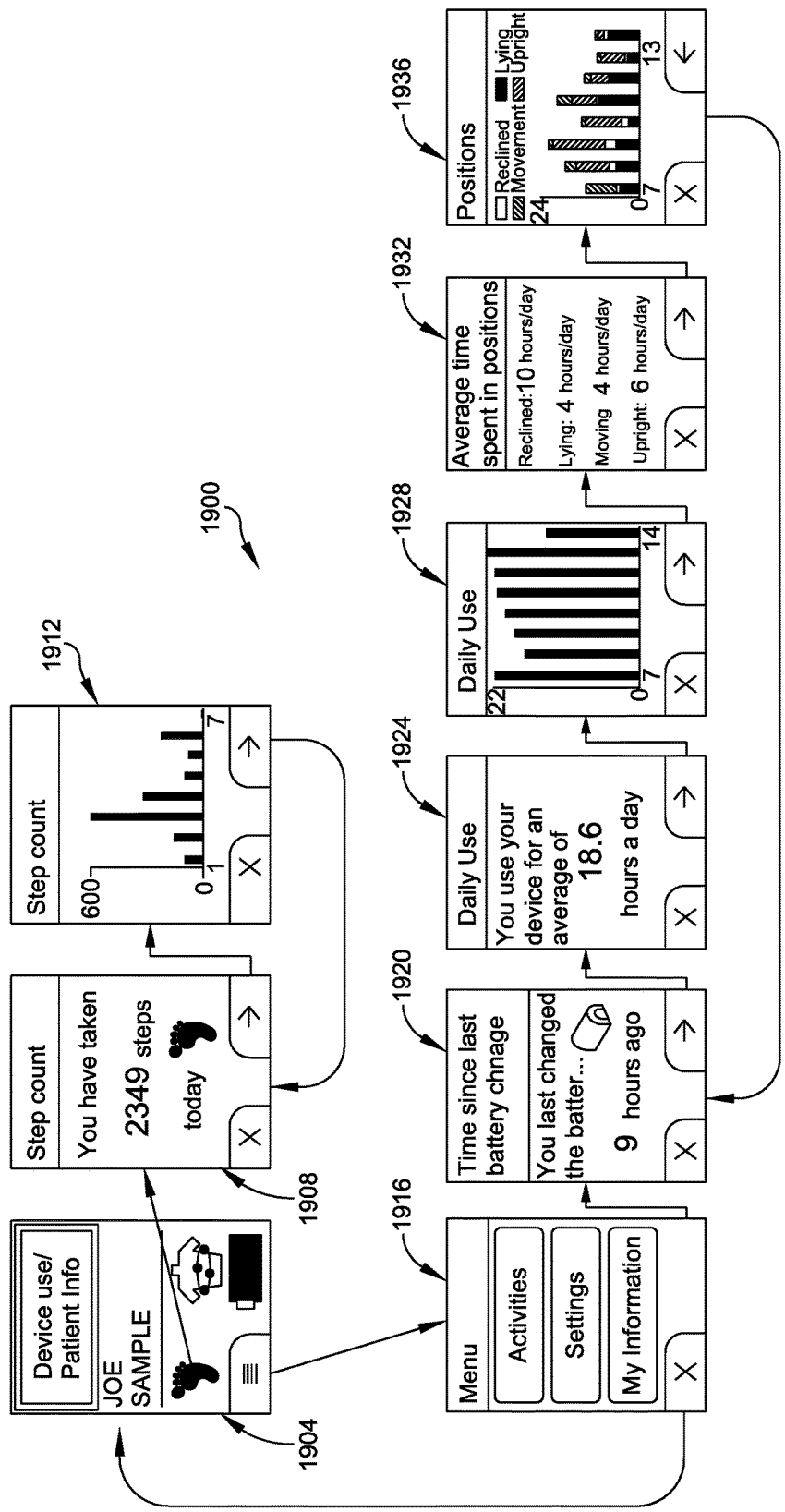
FIG. 19 is an illustration of user interface elements enabling access to and providing patient activity information in accordance with an example of the present disclosure.

FIG. 19 illustrates various examples of one or more selectable elements that the patient activity component may provide via a user interface in some implementations. More particularly, as shown, FIG. 19 includes an icon 1904 and an option button 1916. In some examples, the patient activity component is configured to respond to a selection of the icon 1904 by presenting the first of one or more patient activity reports detailing patient step count information. In some examples, the patient activity component is configured to respond to a selection of the option button 1916 by presenting the first of one or more patient activity reports directed to device use patient position information.

In act 504, the reporting component receives and parses data descriptive of an interaction that indicates a request for a report. Within the act 504, the reporting component may identify the source of the request for the report (e.g., a local or remote user interface) and one or more report options that affect the content of the report. For instance, the reporting component may search for, identify, and retrieve an association stored in a data store (e.g., the operational data store 430) between the interaction and the one or more report options. In some examples, these report options may specify one or more a target recipients of a report, one or more subsystems to include in a device health report, and/or a currency requirement for the operational status information to be included in a device health report. The currency requirement may specify a predefined relationship between the current time and a time when the operational status information was created. The predefined relationship may require, for example, that the creation time of the operational status information be within 24 hours of the current time, although other relationships ranging from 1 hour to 1 week may be used. As described further below in some examples, if the predefined relationship does not exist, the operational status information is inferred to be stale and may be refreshed. Where the interaction is not associated with one or more options, the reporting component may replace any omitted options with one or more default options.

Figure 5:
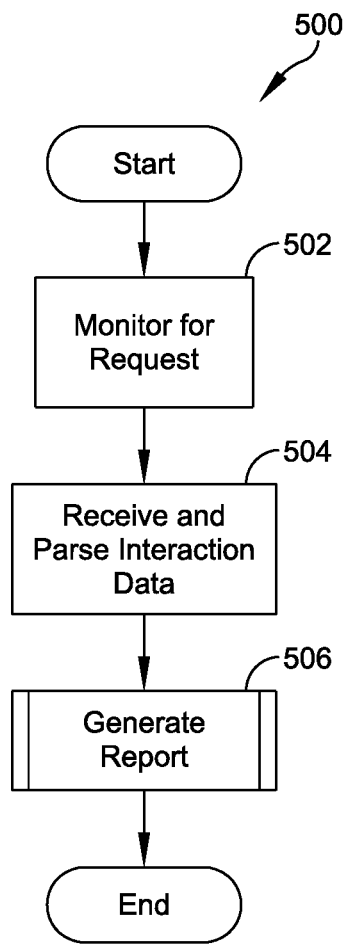
FIG. 5 is a flow diagram illustrating one example of an input handling process in accordance with an example of the present disclosure.

Returning to the input handling process illustrated in FIG. 5, in the act 506, the reporting component generates a report and provides the report to a user interface integral to, or in communication with, the medical device. FIG. 6 illustrates one example of a report generation process 600 executed within the act 506.

The report generating process 600 starts in act 602, where the device health component identifies one or more subsystems to include in the device health report. In some examples, the device health component identifies the one or more subsystems by accessing a report option that specifies the one or more subsystems. In at least one example, the device health component identifies the one or more subsystems by accessing a cross-reference (e.g., the cross-reference 1100) that specifies associations between the one or more subsystems and one or more data sources.

In act 604, the device health component identifies a next subsystem to analyze for operability. In some examples, the device health component makes this identification by accessing the next unprocessed subsystem from the one or more subsystem identified in the act 602.

In act 606, the device health component identifies a next data source to query for operational status information. In some examples, the device health component makes this identification by accessing the next unprocessed record within a subset of the cross-reference. In these examples, the subset of the cross-reference includes only those records that associate data sources with the unprocessed subsystem identified in the act 604.

In act 608, the device health component queries the next data source identified in the act 606 for operational status information. Each data sources may have a distinct access method. Some data sources may be data storage locations that can be accessed by reading operational status information data stored at the location. Other data sources may be accessed via interface calls. Thus, the examples disclosed herein are not limited to a particular data source access method.

Figure 6:
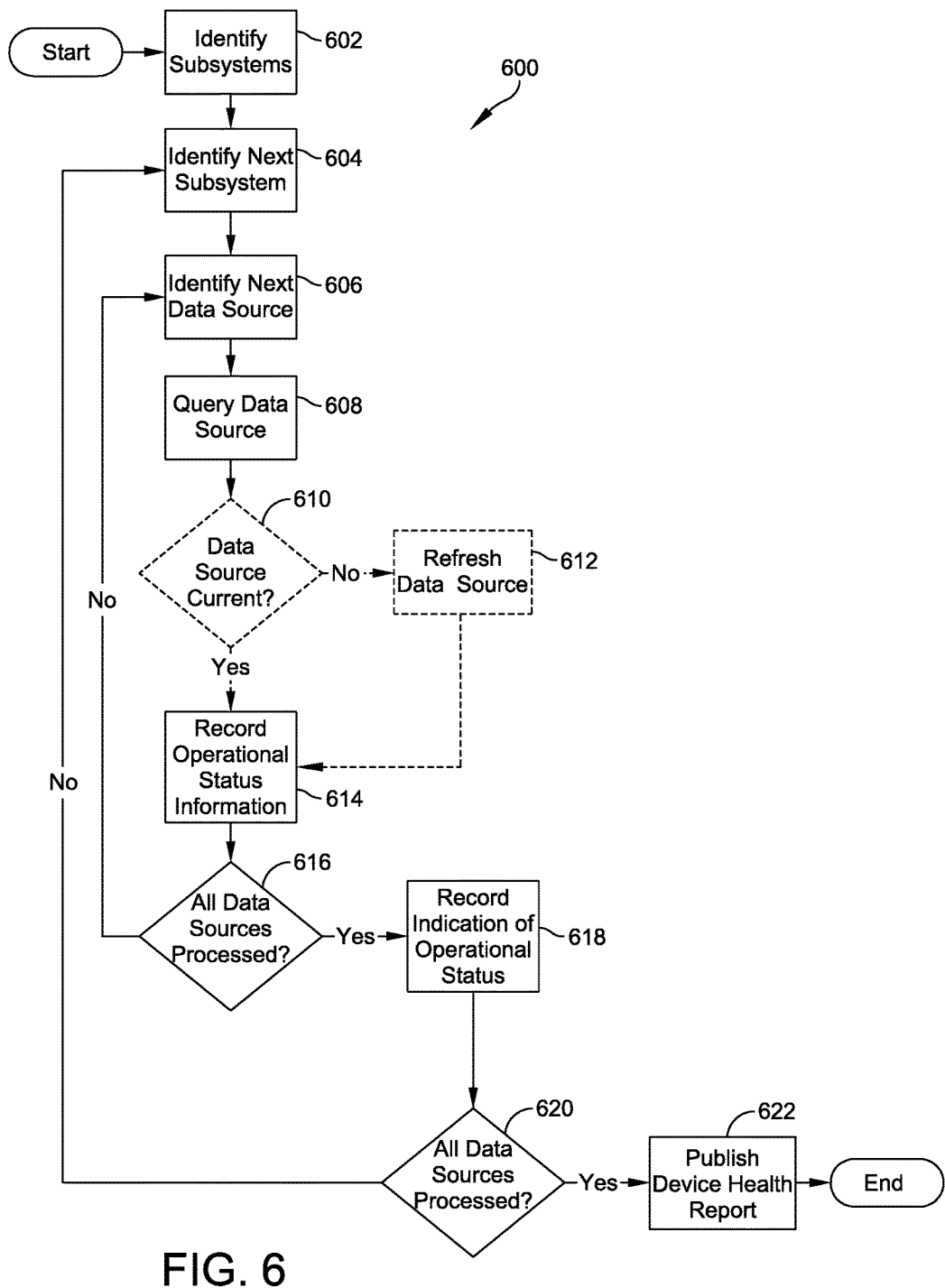
FIG. 6 is a flow diagram illustrating one example of a device health report generation process in accordance with an example of the present disclosure.
Figure 7:
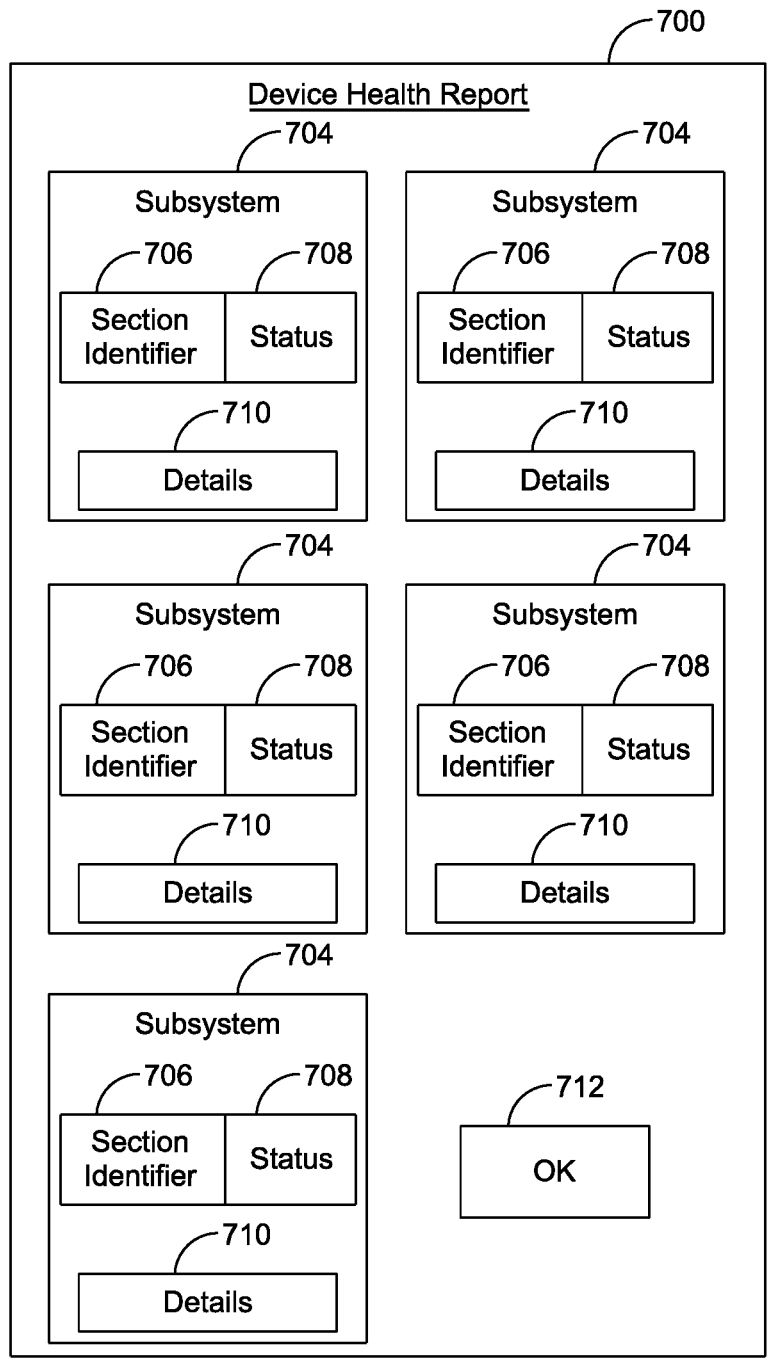
FIG. 7 is a schematic diagram of one example of a device health report in accordance with an example of the present disclosure.

In act 610, which is optional as indicated by its rendering in dashed line form in FIG. 6, the device health component determines whether the operational status information retrieved from one or more data sources is current. For example, the act 610 may be omitted where the source of the request for the device health status report is remote from the medical device. In some examples, the device health component makes this determination by comparing data descriptive of the creation time of the operational status information (e.g., a timestamp) with an associated or default report option that specifies a currency requirement. As described above, the currency requirement may specify a predefined relationship between the current time and the creation time of the operational status information. Where the device health component determines that the current time is not in the predefined relationship with the creation time of the operational status information, the device health component infers that the operational status information is stale and executes act 612. Where the device health component determines that the current time is in the predefined relationship with the creation time of the operational status information, the device health component infers that the operational status information is current and executes act 614.

In the act 612, which is optional as indicated by its rendering in dashed line form in FIG. 6, the device health component attempts to refresh the data source and query the refreshed data source for operational status information. For example, the act 612 may be omitted where the source of the request for the device health status report is remote from the medical device. In some examples, the device health component executes the act 612 by communicating refresh requests to other system components, such as a self-diagnostic component (e.g., the self-diagnostic component 414). In these examples, the device health component does not interfere with the normal operations of the components in a substantial manner. In some examples, where the other system component fails to respond or to refresh the operational status information, the device health component infers that the other system component is not operational and executes the act 614.

In some examples of the act 612, such as where the data source is normally refreshed by the medical device during a power-up process, the device health component prompts the user (e.g., via the user interface) to reboot the medical device and to repeat the request for the device health report. Examples of data sources that are refreshed during the power-up process include the following tests listed in FIG. 11: the microprocessor self-test, the gate array test, the system monitor test, the CRC test, the RAM/ROM test, the watchdog timer test, the removable memory card test, and the user interface test. In other examples of the act 612, such as where the data source is normally refreshed manually on a daily or weekly basis, the device health component prompts the user to refresh the data source. Examples of data sources that are refreshed manually daily or weekly include battery status information based on battery tests, high voltage converter status information based on converter tests, capacitor and/or energy delivery subsystem status information based on capacitor and/or energy deliver subsystem tests, and gel deployment subsystem status information based on gel deployment subsystem tests.

In the act 614, the device health component stores the operational status information acquired in the acts 608 or 612 in the operational data store. In the act 616, the device health component determines whether any of the data sources associated with the unprocessed subsystem remain unprocessed. If any such unprocessed data sources remain, the device health component executes that act 606. If no such unprocessed data sources remain, the device health component executes the act 618.

In the act 618, the device health component records an indication of the operational status of the unprocessed subsystem based on the operational status information regarding the unprocessed subsystem stored in the operational data store. In some examples, the device health component performs a complex set of evaluations and other logic to infer whether the unprocessed subsystem is operational. In other examples, the operational status information indicates whether the identified subsystem is operational without further processing. In any case, the device health component processes the operational status information and stores, in the operational data store, an indication of the operational status of the unprocessed subsystem.

In at 620, the device health component determines whether any of the subsystems identified in the act 602 remain unprocessed. If the device health component determines that any such subsystems remain unprocessed, the device health component executes the act 604. If the device health component determines that no such subsystems remain unprocessed, the device health component executes act 622.

In the act 622, the device health component assembles an instance of the device health report and provides the instance to via user interface. In some examples, the device health component provides this instance of the device health report to a default recipient (e.g., the user interface 408) and/or to other recipients specified by one or more report options. For example, the device health report may display the instance of the device health report to a patient (e.g., the patient 102) via the user interface 408, transmit an email including the instance of the device of health report to an email address associated with a caregiver of the patient (or another person), and/or transmit data descriptive of the instance of the device health report to remote server, such as the remote server 806 described further below with reference to FIG. 8. The report generation 600 ends after execution of the act 622.

Processes in accord with the report generation process 600 enable a medical device to provide timely and accurate information regarding the operational status of the medical device to concerned persons. It is appreciated that the report generation process may be executed as often as need to provide patients and other concerned persons reassurance of the operational integrity of the medical device, thereby decreasing the concerned concern person's reliance on other means for such reassurance (e.g., support staff, caregivers, etc.).

FIG. 7 illustrates a device health report 700 as provided by a device health component (e.g., the device health component 416) in accordance with at least one example. As shown, the device health report 700 includes sections 704, each of which is associated with a different subsystem of a medical device, and an acknowledgment button 712. The number of sections 704 varies with the number of subsystems included in the medical device. In one example, the device health report 700 includes six sections 704 (e.g., a monitor subsystem section 704, an electrode subsystem section 704, a battery subsystem section 704, a base station subsystem section 704, a garment subsystem section 704, and a communications subsystem section 704). The acknowledgment button is selectable to cause the device health component to close the device health report 700. Each section 704 includes a section identifier 706, an operational status indicator 708, and a details button 710. The section identifier 706 of each section 704 includes a textual and/or graphic identifier that summarizes and represents the subsystem associated with the section 704. The section identifier 706 allows a user to quickly understand the subsystem associated with the section 704. Examples of section identifiers include icons, animation, video, and/or text descriptive of a monitor (e.g., the controller 120), a battery, a base station (e.g., the base station 200), a garment (e.g., the garment 110), and/or a graphic of components of a system including the medical device (e.g., the base station 200, the controller 120, and/or the remote server 806, which is described further below). In some examples, each section 704 includes information descriptive of the currency of the data sources referenced to generate the operational status indicator 708 for the section. This information descriptive of the currency may include date/time information and an indication of whether one or more data sources where omitted from processing in generating the indication the operational status indicator 708 for the section.

In some examples, the operational status indicator 708 of each section 704 is an image that summarizes and represents the operational status of the subsystem associated with the section 704. Examples of images that may be used as operational status indicators include checkboxes (e.g. to indicate the subsystem is operational) and boxes with an "X" (e.g. to indicate the subsystem is not operational). In some examples, the checkmarks within the check boxes may be shaded particular colors to indicate the degree of operability of the subsystem. For instance, a green checkmark may include the subsystem is operable and is functioning normally and has no warnings or other indications of future inoperability. A yellow checkmark may indicate the subsystem (or a component thereof) is operable, but is not functioning normally, is nearing the end of its service life, and/or has presented operational status information that indicates a particular, potential future problem that may affect operability. A yellow checkmark may also indicate a changing, transitory, or warning status. In some examples, a yellow checkmark may further indicate that a component or subsystem should be replaced. For instance, in some examples, a yellow checkmark within a garment subsystem section indicates that the garment is approaching 4 months of wear. In at least one example, a yellow checkmark within the battery subsystem section indicates the cell cycle count is approaching 200. A red "X" may indicate the subsystem is not operable. Other colors and/or indicators may be used to indicate these and other operability states and the examples disclosed herein are not limited to a particular color scheme.

In some examples, the details button 710 of each section 704 is selectable to cause the device health component to present, via the device health report 700, additional details regarding the operational status of the subsystem associated with the section 704. These additional details may be, for example, results of one or more tests executed by the self-diagnostic component 414 or other operational status information acquired from a data source. The additional detail may also include troubleshooting information specific to any detected anomalies, historical operational status information covering a user configurable period of time, and compliance information (e.g., last time a battery in the medical device was changed, last time a garment integral to the medical device was laundered, chronology of device wear, etc.). In some examples, the operational status indicator 708 of each section 704 is also selectable to cause the device health component to present the additional details via the device health report 700. Some additional examples of troubleshooting information and processes are described further below with reference to FIGS. 12-15.

In some examples, the device health component and the user interface are configured to render the device health report 700 in an audio format via, for instance, the speaker 304. In these examples, the selectable elements of the device health report 700 take the form of vocal commands that may be detected and processed by the user interface and the device health component.

In some examples, where the user interface includes dedicated elements, such as the LEDs 324 and speaker 322 described above, the device health component is configured to utilize the dedicated elements to convey device health reports. More specifically, in some examples, the device health component is configured to provide operational status indicators, such as those described above with reference to FIG. 7, via the LEDs 324 and/or the speaker 322. In these examples, the device health component may be configured to provide device health reports via the dedicated user interface elements in addition to, or as an alternative to, the screen 320 and the speaker 324.

Figure 12:
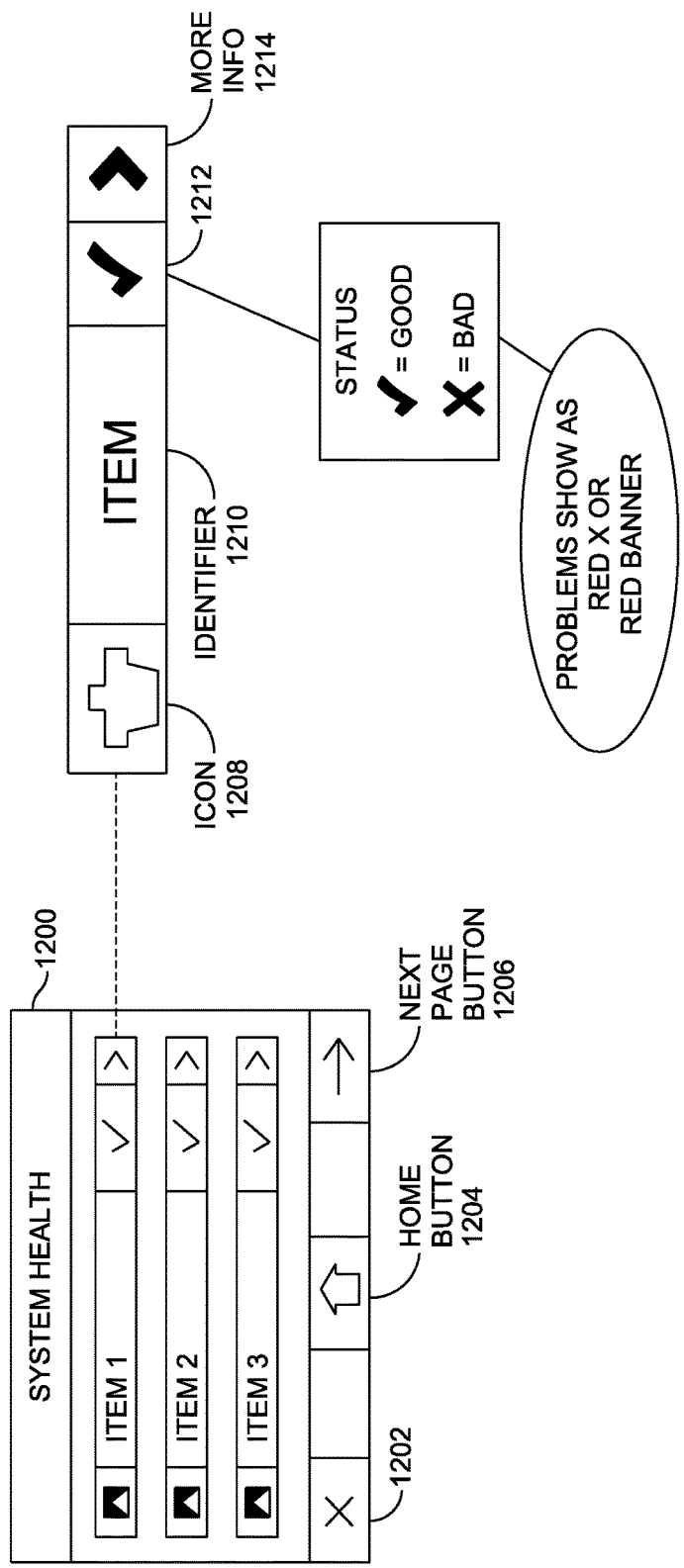
FIG. 12 is an illustration of one example of a device health report in accordance with an example of the present disclosure.

FIG. 12 illustrates another example of a device health report 1200 provided by the device health component in some implementations. As shown, the device health report 1200 includes item sections 1, 2, and 3, a cancel button 1202, a home button 1204, and a next page button 1206. Each item section may correspond to a subsystem or component of the medical device. The cancel button 1202 is selectable to cause the device health component to close the device health report 1200. The home button 1204 is selectable to cause the device health component to navigate the user interface to a predefined home screen (e.g., a top level menu, such as the home screen 1600). The next page button 1206 is selectable to cause the device health component to navigate the user interface to a next page of the device health report 1200 which includes additional item sections.

Each of the item sections includes an icon 1208, an identifier 1210, a status indicator 1212 and a more information button 1214. The icon 1208 includes an image that represents the item that is the subject of the item section. The identifier 1210 includes some identifier (e.g., a word or phrase) of the subject item. The status indicator 1212 indicates an operational status of the subject item. For example, the status indicator 1212 may include a green checkmark to indicate a normal operational status or may include a read "X" or banner to indicate an operational status that is anomalous or non-operational. The more information button 1214 is selectable to cause the device health component to "drill down" into the device health report 1200 by displaying additional information regarding the reported status of the subject item.

Figure 13:
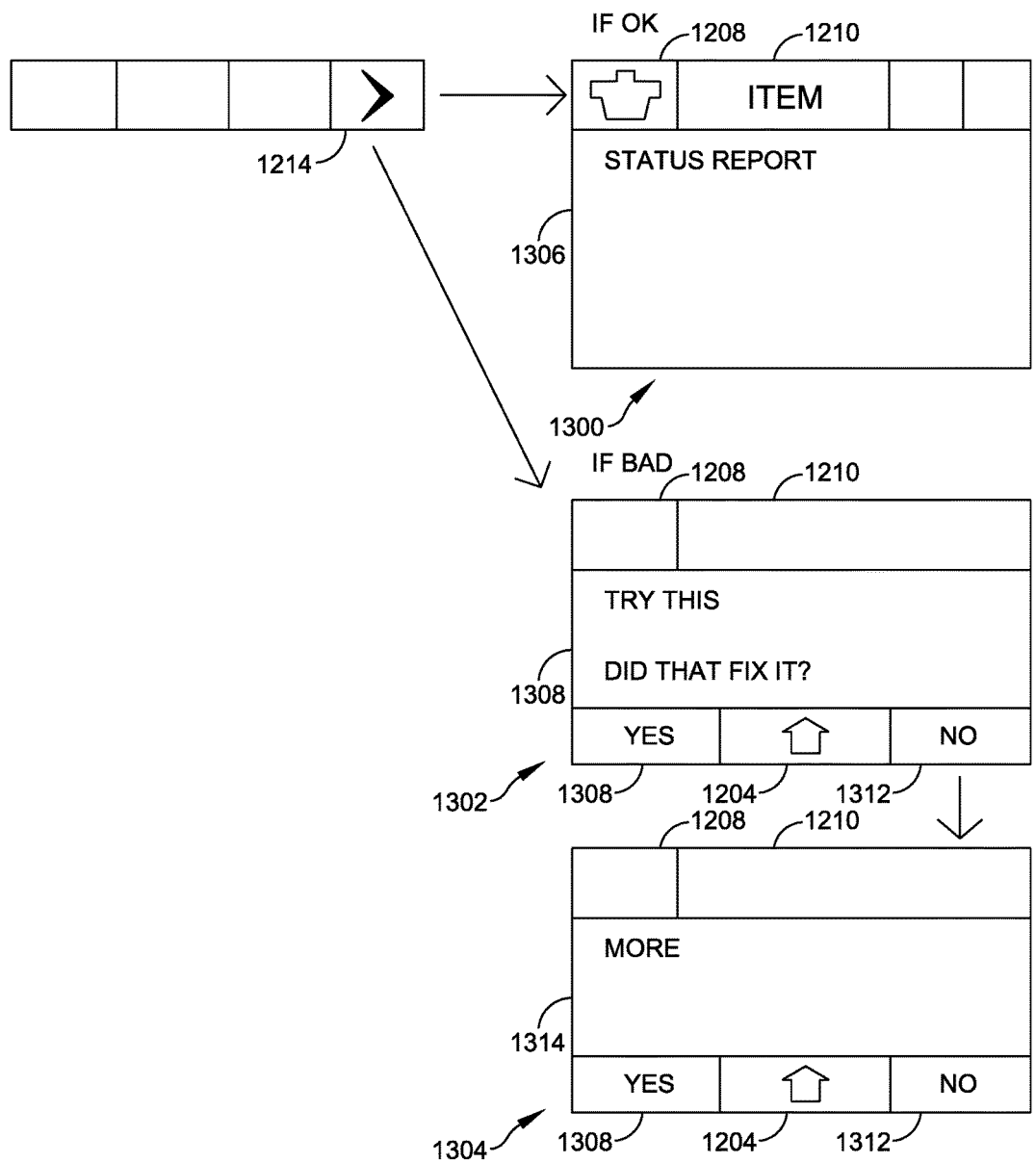
FIG. 13 is an illustration of user interface elements presented within a device health report in accordance with an example of the present disclosure.

FIG. 13 illustrates the operations initiated by the more information button 1214 according to one implementation. As shown in FIG. 13, in response to a selection of the more information button 1214, the device health component determines whether the operational status of the subject item is normal or anomalous. Where the operational status of the subject item is normal, the device health component displays the screen 1300. Where the operational status of the subject item is anomalous, the device health component displays the screen 1302. The screen 1300 displays the icon 1208 and the identifier 1210 of the subject item and a status report 1306 descriptive of the operational status of the subject item.

The screen 1302 displays the icon 1208 and the identifier 1210 of the subject item, troubleshooting information 1308, a yes button 1310, a home button 1204, and a no button 1314. The troubleshooting information 1308 describes one or more actions the user viewing the screen 1302 may take to correct the anomalous operational status of subject item. The yes button 1308 is selectable to cause the device health component to record information indicating that the troubleshooting action described by the troubleshoot information 1308 was successful in correcting the anomalous operational status of the subject item. In some examples, selection of the yes button 1308 causes the device health component to refresh the data source associated with the subject item to verify that the subject item is operating normally. The no button 1312 is selectable to cause the device health component to record information indicating that the troubleshooting action described by the troubleshoot information 1308 was not successful in correcting the anomalous operational status of the subject item. In some examples, selection of the no button 1312 causes the device health component to refresh the data source associated with the subject item to verify that the subject item is in an anomalous operational status. In some examples, selection of the no button 1312 also causes the device health component to display the screen 1304.

The screen 1304 displays the icon 1208 and the identifier 1210 of the subject item, additional troubleshooting information 1314, a yes button 1310, a home button 1204, and a no button 1314. The additional troubleshooting information 1314 describes one or more actions the user viewing the screen 1302 may take to correct the anomalous operational status of subject item. For example, the trouble shooting information 1308 may be directed to the most likely cause of the anomalous operational status of the subject item and the additional troubleshooting information 1314 may be directed to the next most likely cause of the anomalous operational status of the subject item.

Figure 14:
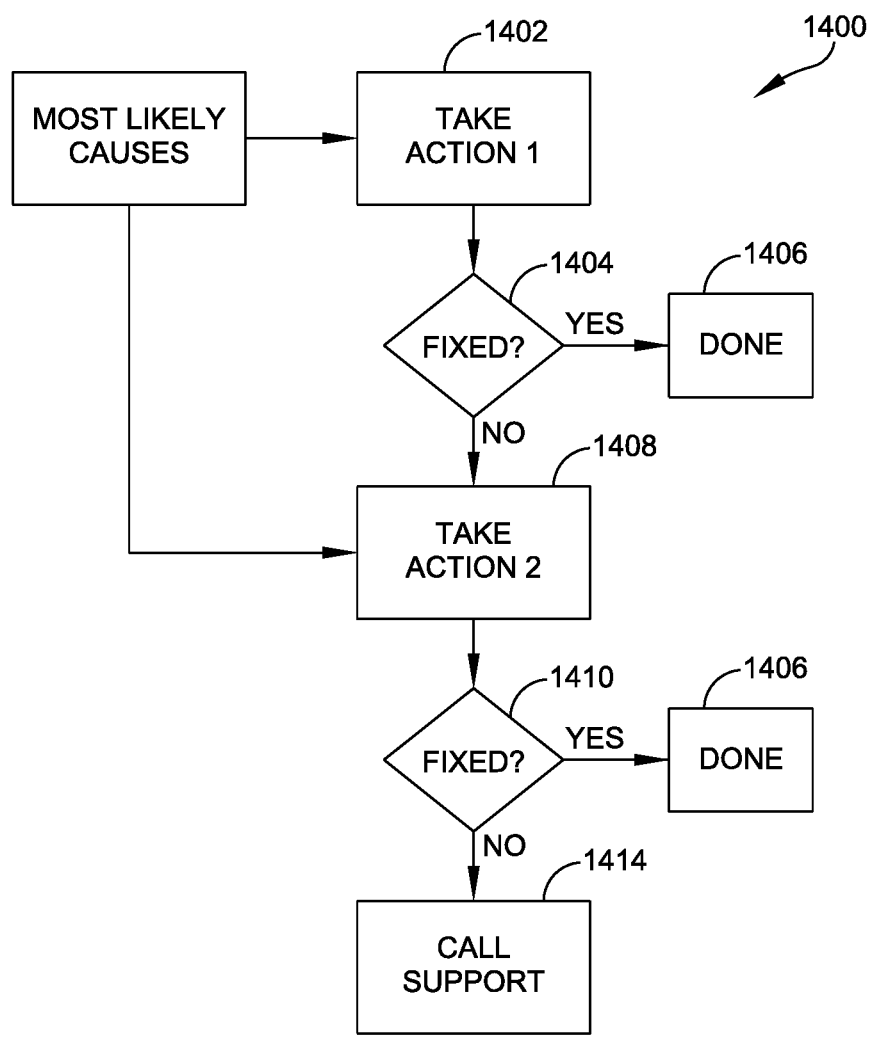
FIG. 14 is a flow diagram illustrating one example of a troubleshooting process in accordance with an example of the present disclosure.

In some examples, the device health component implements a troubleshooting process via screens such as 1308 and 1314. FIG. 14 illustrates a troubleshooting process 1400 available in some implementations. The troubleshooting process 1400 begins with act 1402 where the device health component renders first troubleshooting information directed to a most likely cause of the anomalous state reported for a subject item. For example, this first troubleshooting information may be displayed in a device health report. In act 1404, the device health component determines whether the anomalous operational status reported for the subject item persists. This action may be accomplished by receiving a "yes" or a "no" from selection of the yes button 1310 or the no button 1312. This action may also be accomplished by refreshing a data source associated with the subject item. Where the operational status of the subject item is normal, the device health component executes act 1406. Where the operational status of the subject item remains anomalous, the device health component executes act 1408.

In the act 1406, the device health component records an audit trail descriptive of the current instance of the troubleshooting process 1400 and terminates the troubleshooting process 1400. In some examples, the device health component utilizes this audit trail to reestablish the troubleshooting process 1400 where, for example, the troubleshooting information displayed in either the act 1402 or act 1408 includes a prompt to reboot the medical device and the user complies with the prompt.

In the act 1408, the device health component renders second troubleshooting information directed to a next most likely cause of the anomalous state reported for the subject item. For example, this first troubleshooting information may be displayed in a device health report. In act 1410, the device health component determines whether the anomalous operational status reported for the subject item persists. Where the operational status of the subject item is normal, the device health component executes act 1406. Where the operational status of the subject item remains anomalous, the device health component executes act 1414.

In the act 1414, the device health component prompts the user viewing the device health report 1200 to call a support representative. This prompt may include a telephone number or additional contact information for the support representative. Additionally, in some examples, the prompt is selectable to cause the device health component to establish an interactive communication session with the support representative, as described above with reference to FIG. 18.

Figure 15:
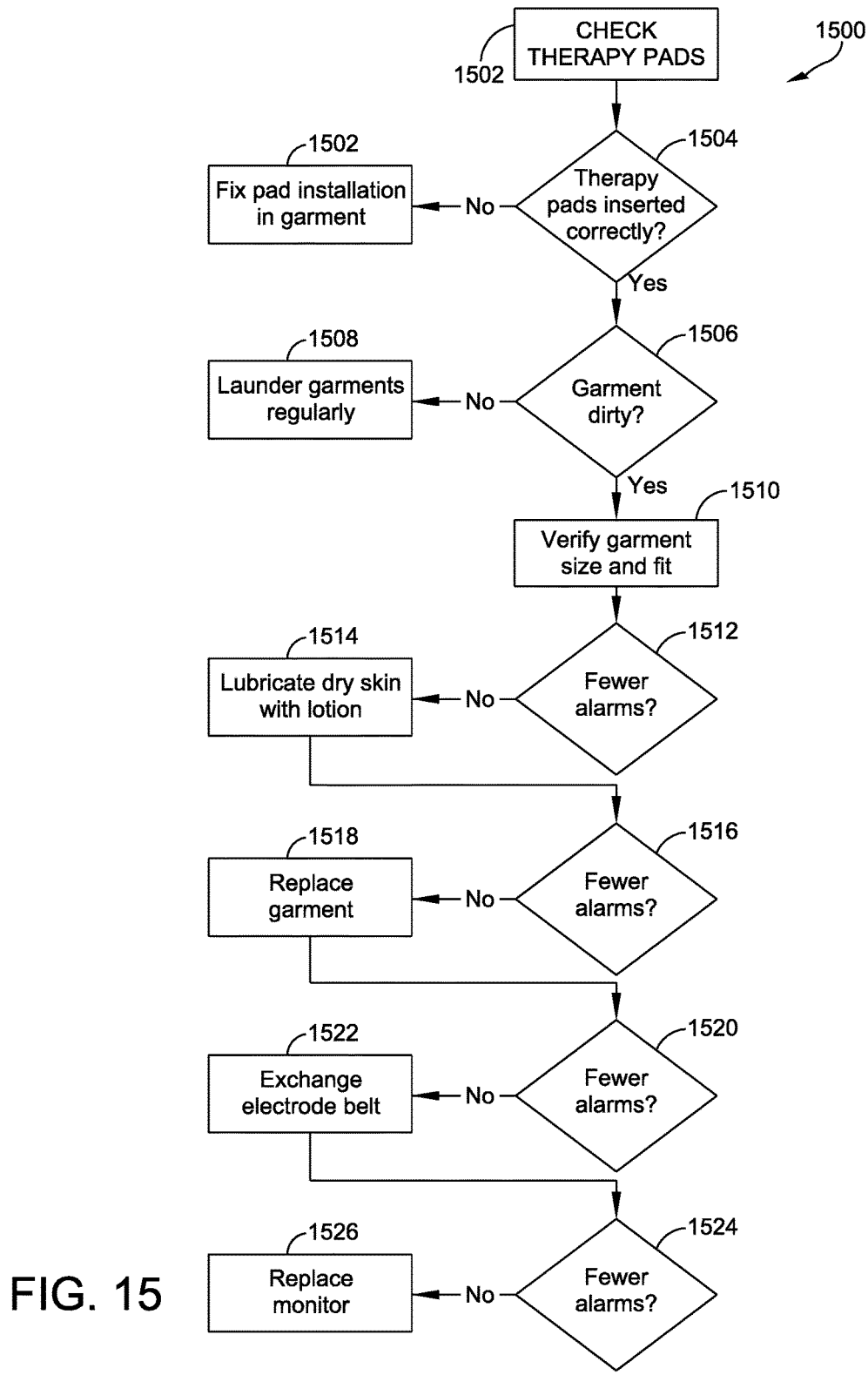
FIG. 15 is a flow diagram illustrating another example of a troubleshooting process in accordance with an example of the present disclosure.

FIG. 15 illustrates another troubleshooting process 1500 executed by the device health component in some implementations. The troubleshooting process 1500 is specific to a garment subsystem of a wearable defibrillator. The troubleshooting process 1500 iterates through a series of prompts presented to a user viewing a device health report (e.g., the device health report 700 or the device health report 1200). As shown, the troubleshooting process 1500 begins at act 1502 where the device health component prompts the user to check the therapy electrodes of the wearable defibrillator to determine whether the therapy electrodes are positioned properly with a garment housing the therapy electrodes. In the act 1504, the device health component determines whether the therapy electrodes are properly positioned. This determination may be made based on user input (e.g., selection of a yes button or a no button) or a refreshed data source. Where the therapy electrodes are properly positioned, the device health component executes the act 1506. Where the therapy electrodes are not properly positioned, the device health component executes the act 1502.

In the act 1502, the device health component prompts the user to fix the therapy electrodes in the garment. In some examples, the user removes the battery of the medical device as part of complying with this prompt. In these examples, the device health component reestablishes the troubleshooting process 1500 at the act 1502 upon completion of the power-up process. The device health component may perform this reestablishment with reference to an audit trail maintained by the device health component. In the act 1506, the device health component prompts the user to determine whether the garment is dirty and determines whether the garment is dirty based on a response from the user. Where the garment is dirty, the device health component executes the act 1508. Where the garment is not dirty, the device health component executes the act 1510.

In the act 1508, the device health component prompts the user to launder the garment regularly. In the act 1510, the device health component prompts the user to determine whether the garment is sized and fitted properly.

In the act 1512, the device health component determines whether fewer false alarms have been raised over a predetermined, configurable period of time by reviewing an alarm history stored in an operational data store (e.g., the operational data store 430). Where there are non-zero false alarm instances and the false alarm instances are not trending downward, the device health component prompts the user to lubricate the patient's skin with lotion in act 1514.

In the act 1516, the device health component determines whether fewer false alarms have been raised over a predetermined, configurable period of time by reviewing an alarm history stored in the operational data store. Where there are non-zero false alarm instances and the false alarm instances are not trending downward, the device health component prompts the user to replace the garment in act 1518.

In the act 1520, the device health component determines whether fewer false alarms have been raised over a predetermined, configurable period of time by reviewing an alarm history stored in the operational data store. Where there are non-zero false alarm instances and the false alarm instances are not trending downward, the device health component prompts the user to replace the belt of the medical device in act 1522.

In the act 1524, the device health component determines whether fewer false alarms have been raised over a predetermined, configurable period of time by reviewing an alarm history stored in the operational data store. Where there are non-zero false alarm instances and the false alarm instances are not trending downward, the device health component prompts the user to replace the monitor of the medical device in act 1526 and terminates the troubleshooting process 1500.

It is appreciated that the troubleshooting processes 1400 and 1500 may be repeated as many times and as often as needed to maintain normal operation of the medical device and peace of mind for the patient. Additionally, while the example of the troubleshooting process 1400 depicted in FIG. 14 includes display of first and second troubleshooting information, the examples disclosed herein are not limited to two instances of troubleshooting information and one, three or more instances of troubleshooting information may be provided.

Example Patient Activity Report Processes

As described above, in some implementations, in addition or instead of device operational status information, the patient is able to view one or more patient activity reports, such as a device use report and/or patient information report. For example, such reports may include details regarding the patient's use of the device. For example, such reports may include details regarding patient statistics, trends, compliance with device use instructions and/or guidelines provided to the patient, and other vital signs data. Referring to FIG. 19, device use and/or patient trend information 1900 that is available to the patient via a user interface of the medical device is shown. For example, as shown when the patient clicks on icon 1904, the patient is presented with details 1908 regarding a number of steps taken by the patient while wearing the device. The patient is also able to view more detailed step count information 1912.

Device use information may include information about a patient's use of the device. For example, such information may be provided to the patient as shown in screens 1916-1936. Such information may include information about a patient's compliance with instructions of use of the medical device, e.g., an amount of time that the patient' wears or uses the device as instructed by his or her physician, when the patient changes the device batteries, and performs other required device maintenance, etc. As shown, the patient may click on an option featuring the patient's information (e.g., My Information) 1916 to view details regarding when the patient last changed the device battery 1920, a daily time of wear of the device 1924-1928 and an average time spent by the patient in various positions 1932-1936. Other information that may be presented to the patient in the manner described above (e.g., via device use and/or patient trend information 1900) may include ECG information, heart rate information and trends, blood oxygen levels, tissue fluid levels, etc.

The processes disclosed herein each depict one particular sequence of acts in a particular example. The acts included in these processes may be performed by, or using, one or more computer systems specially configured as discussed herein. Some acts are optional and, as such, may be omitted in accord with one or more examples. Additionally, the order of acts can be altered, or other acts can be added, without departing from the scope of the systems and methods discussed herein. Furthermore, as discussed above, in at least one example, the acts are performed on a particular, specially configured machine, namely a medical device configured according to the examples disclosed herein.

Device Report Distribution Systems

A medical device including a device health component (e.g., the device health component 416) may be incorporated into a report distribution system that provides multiple points of access to device health reports. FIG. 8 illustrates a report distribution system 800 in accordance with some of these examples. As shown, the report distribution system 800 includes a medical device 802, a programmable device 804, a remote server 806, and a communication network 808. The medical device 802 exchanges (i.e., transmits or receives) information with the remote server 806 via the network 808. Similarly, the programmable device 804 may exchange information with the remote server 806 via the network 808. The network 808 may include any communication network through which programmable devices may exchange information. In some examples, the network 808 supports wireless network and/or wired connections. For instance, the network 808 may support any of various networking standards such as GSM, CMDA, USB, BLUETOOTH, CAN, ZigBee, Wireless Ethernet, and TCP/IP among others.

The medical device 802 may include any medical device disclosed herein or a different medical device that includes a device health component. In one example illustrated by FIG. 8, the medical device 802 is associated with and provides care to a patient 102. In various examples, the programmable device 804 is implemented using any of a variety of programmable devices (e.g., a device with data storage and at least one processor in data communication with the data storage). In some examples, the programmable device 804 includes a plurality of interfaces, one or more processors, and a data storage device coupled to one another via a communication mechanism, such as a bus. In these examples, the programmable device 804 also includes a battery to power the device and may include one or more antennas. The plurality of interfaces in the programmable device 804 includes a user interface, and a network interface configured to communicate with the network 808.

As shown in FIG. 8, the medical device 802 may provide information to the patient 102 and/or another user 810 (e.g., a support technician, a caregiver, etc.). In some examples, the programmable device 804 is also associated with and provides information to the patient 102 and/or the user 810. For example, the programmable device 804 may be a base station placed in the patient's home or other convenient location, e.g., similar to the base station 200 shown in and described in connection with FIG. 2.

In some examples, the device health component is configured (e.g., via one or more report options specifying one or more recipients) to transmit instances of a device health report and/or a patient activity report (device use reports and/or patient information reports) to the remote server 806 via the network 808. In these examples, the patient 102 and/or the user 802 may access these health care report instances via the programmable device 804. For example, the programmable device 804 may include a specialized app, browser, email client, or some other local component configured to communicate with the remote server 806 via the network 808. In another example, the device health component is configured to transmit instances of the device health report directly to the programmable device via the network 808. In these ways, the report distribution system provides remote access to device health reports for interested persons.

Particular examples of the programmable device 804 include medical devices (e.g., in FIG. 8, medical devices other than medical device 802), wearable devices, medical device chargers, medical device base stations, smart phones, tablet computers, and laptop computers. Wearable devices that may serve as the programmable device 804 include various garments with integrated technologies, watches, anklets, necklaces, belt buckles, and glasses.

Having thus described several aspects of at least one example, it is to be appreciated that various alterations, modifications, and improvements will readily occur to those skilled in the art. For instance, examples disclosed herein may also be used in other contexts. Such alterations, modifications, and improvements are intended to be part of this disclosure, and are intended to be within the scope of the examples discussed herein. Accordingly, the foregoing description and drawings are by way of example only.

The invention claimed is:

1. An ambulatory medical device comprising a plurality of subsystems, the ambulatory medical device comprising:
   a garment to be worn by an ambulatory patient, the garment comprising
      at least one electrocardiogram (ECG) electrode that is disposed externally on the ambulatory patient's body, the at least one ECG electrode configured to acquire ECG data descriptive of the ambulatory patient's cardiac activity and indicative of whether the ambulatory patient is experiencing a life-threatening cardiac arrhythmia, and
      at least one therapy electrode that is positioned external to the ambulatory patient's body, the at least one therapy electrode configured to provide one or more therapeutic defibrillating or pacing shocks to the ambulatory patient when the ambulatory patient is experiencing the life-threatening cardiac arrhythmia; and
   a controller comprising
      a user interface, and
      at least one processor disposed in the controller and coupled to the at least one ECG electrode, the at least one therapy electrode, and the user interface, and configured to
         execute a plurality of self-diagnostic tests to evaluate operational integrity of each of the plurality of subsystems of the ambulatory medical device, the plurality of self-diagnostic tests comprising at least
            an ECG signal quality test of the at least one ECG electrode,
            an ECG falloff test for the at least one ECG electrode, and
            an operational test of the at least one therapy electrode,
         produce test results indicative of the operational integrity of each of the plurality of subsystems, the test results comprising results of the ECG signal quality test of the at least one ECG electrode, the ECG falloff test for the at least one ECG electrode, and the operational test of the at least one therapy electrode,
         identify subsystem status information descriptive of an operational status of the at least one ECG electrode based on the ECG signal quality test and the ECG falloff test,
         identify subsystem status information descriptive of an operational status of the at least one therapy electrode based on the operational test of the at least one therapy electrode, and
         provide a device health report for the ambulatory medical device to the ambulatory patient via the user interface, the device health report comprising
            (a) a first indication of whether the at least one ECG electrode that is disposed externally on the ambulatory patient's body is in an operational state or a nonoperational state as determined based upon the ECG signal quality test of externally detected ECG signals,
            (b) a second indication of whether a signal quality of externally detected ECG signals is compromised as determined based on the ECG falloff test, and
            (c) a third indication of whether the at least one therapy electrode that is positioned external to the ambulatory patient's body is in an operational state or a nonoperational state as determined based upon the operational test.

2. The ambulatory medical device of claim 1, wherein the plurality of subsystems comprises at least one of a monitor subsystem, a sensing electrode subsystem comprising the at least one ECG electrode, a therapy electrode subsystem, a battery subsystem, a base station subsystem, a garment subsystem, and a communications subsystem.

3. The ambulatory medical device of claim 2, wherein the base station subsystem comprises a battery charger subsystem and a base station user interface subsystem.

4. The ambulatory medical device of claim 1, wherein the device health report is configured to notify a user whether (a) the at least one ECG electrode is in the operational state or the nonoperational state based on the first indication, and (b) the at least one therapy electrode is in the operational state or the nonoperational state based on the third indication.

5. The ambulatory medical device of claim 1, wherein the device health report comprises one or more visual user interface elements that provide one or more visual indications of whether (a) the at least one ECG electrode sensor is in the operational state or the nonoperational state based on the first indication, and (b) the at least one therapy electrode is in the operational state or the nonoperational state based on the third indication.

6. The ambulatory medical device of claim 5, wherein the one or more visual user interface elements comprise selectable visual user interface elements configured to receive input from a user.

7. The ambulatory medical device of claim 1, wherein the user interface comprises an audio output component and the device health report is configured to be rendered in audio format via the audio output component.

8. The ambulatory medical device of claim 1, wherein the device health report comprises at least one of icons, animation, video, and textual information relating to a corresponding one of the plurality of the subsystems.

9. The ambulatory medical device of claim 1, wherein the user interface is integral to a remote device distinct from the ambulatory medical device.

10. The ambulatory medical device of claim 1, wherein the user interface comprises an email client.

11. A report distribution system comprising:
a remote server; and
an ambulatory medical device comprising a plurality of subsystems, the ambulatory medical device comprising
a garment to be worn by an ambulatory patient, the garment comprising
at least one electrocardiogram (ECG) electrode that is disposed externally on the ambulatory patient's body, the at least one ECG electrode configured to acquire ECG data descriptive of the ambulatory patient's cardiac activity and indicative of whether the ambulatory patient is experiencing a life-threatening cardiac arrhythmia, and
at least one therapy electrode that is positioned external to the ambulatory patient's body, the at least one therapy electrode configured to provide one or more therapeutic defibrillating shocks or pacing to the ambulatory patient when the ambulatory patient is experiencing the life-threatening cardiac arrhythmia, and
a controller comprising
a network interface configured to couple to and communicate with the remote server, and
at least one processor disposed in the controller and coupled to the at least one ECG electrode, the at least one therapy electrode, and the network interface, and configured to
execute a plurality of self-diagnostic tests to evaluate operational integrity of each of the plurality of subsystems of the ambulatory medical device, the plurality of self-diagnostic tests comprising at least
an ECG signal quality test of the at least one ECG electrode,
an ECG falloff test for the at least one ECG electrode, and an operational test of the at least one therapy electrode,
produce test results indicative of the operational integrity of each of the plurality of subsystems, the test results comprising results of the ECG signal quality test of the at least one ECG electrode, the ECG falloff test for the at least one ECG electrode, and the operational test of the at least one therapy electrode,
identify subsystem status information descriptive of an operational status of the at least one ECG electrode based on the ECG signal quality test and the ECG falloff test,
identify subsystem status information descriptive of an operational status of the at least one therapy electrode based on the operational test of the at least one therapy electrode, and
provide a device health report for the ambulatory medical device to at least one of the ambulatory patient via a user interface and the remote server via the network interface, the device health report comprising (a) a first indication of whether the at least one ECG electrode that is disposed externally on the ambulatory patient's body is in an operational state or a nonoperational state as determined based upon the ECG signal quality test of externally detected ECG signals,
(b) a second indication of whether a signal quality of externally detected ECG signals is compromised as determined based on the ECG falloff test, and
(c) a third indication of whether the at least one therapy electrode that is positioned external to the ambulatory patient's body is in an operational state or a nonoperational state as determined based upon the operational test.

12. The report distribution system of claim 11, wherein the plurality of subsystems comprises at least one of a monitor subsystem, a sensing electrode subsystem comprising the at least one ECG electrode, a therapy electrode subsystem, a battery subsystem, a base station subsystem, a garment subsystem, and a communications subsystem.

13. The report distribution system of claim 12, wherein the base station subsystem comprises a battery charger subsystem and a base station user interface subsystem.

14. The report distribution system of claim 11, wherein the device health report is configured to notify a user whether (a) the at least one ECG electrode is in the operational state or the nonoperational state based on the first indication, and (b) the at least one therapy electrode is in the operational state or the nonoperational state based on the third indication.

15. The report distribution system of claim 11, wherein the device health report comprises one or more visual user interface elements that provide one or more visual indications of whether (a) the at least one ECG electrode is in the operational state or the nonoperational state based on the first indication, and (b) the at least one therapy electrode is in the operational state or the nonoperational state based on the third indication.

16. The report distribution system of claim 15, wherein the one or more visual user interface elements comprise selectable visual user interface elements configured to receive input from a user.

17. The report distribution system of claim 11, wherein the user interface comprises an audio output component and the device health report is configured to be rendered in audio format via the audio output component.

18. The report distribution system of claim 11, wherein the device health report comprises at least one of icons, animation, video, and textual information relating to a corresponding one of the plurality of the subsystems.

19. The report distribution system of claim 11, wherein the user interface is integral to a remote device distinct from the ambulatory medical device, the remote device being configured to communicate with at least one of the ambulatory medical device and the remote server.

20. The report distribution system of claim 19, wherein the user interface comprises an email client.

21. A method of providing status information for an ambulatory medical device comprising a plurality of subsystems, the method comprising:
monitoring, by a processor coupled to at least one electrocardiogram (ECG) electrode that is disposed externally on an ambulatory patient's body, ECG data descriptive of the ambulatory patient's cardiac activity and indicative of whether the ambulatory patient is experiencing a life-threatening cardiac arrhythmia;

initiating, by the processor, one or more therapeutic defibrillating or pacing shocks to the ambulatory patient as needed when the ambulatory patient is experiencing the life-threatening cardiac arrhythmia via at least one therapy electrode that is positioned external to the ambulatory patient's body and that is coupled to the processor;

executing, by the processor, a plurality of self-diagnostic tests to evaluate operational integrity of each of the plurality of subsystems of the ambulatory medical device, the plurality of self-diagnostic tests comprising at least
  an ECG signal quality test of the at least one ECG electrode,
  an ECG falloff test for the at least one ECG electrode, and
  an operational test of the at least one therapy electrode;

producing, by the processor, test results indicative of the operational integrity of each of the plurality of subsystems, the test results comprising results of the ECG signal quality test of the at least one ECG electrode, the ECG falloff test of the at least one ECG electrode, and the operational test of the at least one therapy electrode;

identifying, by the processor, subsystem status information descriptive of an operational status of the at least one ECG electrode based on the ECG signal quality test and the ECG falloff test, identifying subsystem status information descriptive of an operational status of the at least one therapy electrode based on the operational test of the at least one therapy electrode; and providing, by the processor, a device health report for the ambulatory medical device to the ambulatory patient via a user interface, the device health report comprising
  (a) a first indication of whether the at least one ECG electrode that is disposed externally on the ambulatory patient's body is in an operational state or a nonoperational state as determined based upon the ECG signal quality test of externally detected ECG signals,
  (b) a second indication of whether a signal quality of externally detected ECG signals is compromised as determined based on the ECG falloff test, and
  (c) a third indication of whether the at least one therapy electrode that is positioned external to the ambulatory patient's body is in an operational state or a nonoperational state as determined based upon the operational test.

22. The method of claim 21, wherein providing the device health report comprises providing operational status information descriptive of at least one of a monitor subsystem, a sensing electrode subsystem comprising the at least one ECG electrode, a therapy electrode subsystem, a battery subsystem, a base station subsystem, a garment subsystem, and a communications subsystem.

23. The method of claim 22, wherein providing the operational status information comprises providing operational status information descriptive of at least one of a battery charger subsystem, the sensing electrode subsystem, the therapy electrode subsystem, a gel deployment subsystem, a sensor interface, a therapy delivery interface, a processing subsystem, and an energy storage and delivery subsystem.

24. A non-transitory computer readable medium storing computer executable instructions to execute a method of providing status information for an ambulatory medical device comprising a plurality of subsystems, the computer executable instructions including instructions to:
  monitor ECG data descriptive of an ambulatory patient's cardiac activity and indicative of whether the ambulatory patient is experiencing a life-threatening cardiac arrhythmia as acquired by at least one electrocardiogram (ECG) electrode that is disposed externally on the ambulatory patient's body;
  initiate one or more therapeutic defibrillating or pacing shocks to the ambulatory patient as needed when the ambulatory patient is experiencing the life-threatening cardiac arrhythmia via at least one therapy electrode that is positioned external to the ambulatory patient's body;
  execute a plurality of self-diagnostic tests to evaluate operational integrity of each of the plurality of subsystems of the ambulatory medical device, the plurality of self-diagnostic tests comprising at least
    an ECG signal quality test of the at least one ECG electrode,
    an ECG falloff test for the at least one ECG electrode, and
    an operational test of the at least one therapy electrode;
  produce test results indicative of the operational integrity of each of the plurality of subsystems, the test results comprising results of the ECG signal quality test of the at least one ECG electrode, the ECG falloff test of the at least one ECG electrode, and the operational test of the at least one therapy electrode;
  identify subsystem status information descriptive of an operational status of the at least one ECG electrode based on the ECG signal quality test and the ECG falloff test, identify subsystem status information descriptive of an operational status of the at least one therapy electrode based on the operational test of the at least one therapy electrode; and
  provide a device health report for the ambulatory medical device to the ambulatory patient via a user interface, the device health report comprising
    (a) a first indication of whether the at least one ECG electrode that is positioned proximate to the ambulatory patient's body is in an operational state or a nonoperational state as determined based upon the ECG signal quality test of externally detected ECG signals,
    (b) a second indication of whether a signal quality of externally detected ECG signals is compromised as determined based on the ECG falloff test, and
    (c) a third (b) an indication of whether the at least one therapy electrode that is disposed externally on the ambulatory patient's body is in an operational state or a nonoperational state as determined based upon the operational test.

25. The computer readable medium of claim 24, wherein the instructions to provide the device health report comprise instructions to provide operational status information descriptive of at least one of a monitor subsystem, a sensing electrode subsystem comprising the at least one ECG electrode, a therapy electrode subsystem, a battery subsystem, a base station subsystem, a garment subsystem, and a communications subsystem.

26. The computer readable medium of claim 25, wherein the instructions to provide the operational status information comprise instructions to provide operational status information descriptive of at least one of a battery charger subsystem, the sensing electrode subsystem, the therapy electrode subsystem, a gel deployment subsystem, a sensor interface, a therapy delivery interface, a processing subsystem, and an energy storage and delivery subsystem.

\* \* \* \* \*